United States Patent
Bollag et al.

(10) Patent No.: US 11,384,142 B2
(45) Date of Patent: Jul. 12, 2022

(54) COMBINATION THERAPY FOR THE TREATMENT OF OVARIAN CANCER

(71) Applicant: Hoffmann-La Roche Inc., Little Falls, NJ (US)

(72) Inventors: David Bollag, Basel (CH); Corrado Bernasconi, Zurich (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/153,637

(22) Filed: May 12, 2016

(65) Prior Publication Data
US 2016/0289317 A1    Oct. 6, 2016

Related U.S. Application Data

(63) Continuation of application No. 14/384,863, filed as application No. PCT/EP2013/054818 on Mar. 11, 2013, now abandoned.

(60) Provisional application No. 61/610,128, filed on Mar. 13, 2012, provisional application No. 61/653,598, filed on May 31, 2012, provisional application No. 61/672,987, filed on Jul. 18, 2012.

(51) Int. Cl.
| | |
|---|---|
| *C07K 16/22* | (2006.01) |
| *A61K 31/4745* | (2006.01) |
| *A61K 31/704* | (2006.01) |
| *A61K 31/337* | (2006.01) |
| *A61K 45/06* | (2006.01) |
| *A61K 9/127* | (2006.01) |
| *A61K 39/395* | (2006.01) |
| *A61K 39/00* | (2006.01) |
| *G06Q 30/02* | (2012.01) |
| *G06Q 90/00* | (2006.01) |

(52) U.S. Cl.
CPC .......... *C07K 16/22* (2013.01); *A61K 9/1271* (2013.01); *A61K 31/337* (2013.01); *A61K 31/4745* (2013.01); *A61K 31/704* (2013.01); *A61K 39/3955* (2013.01); *A61K 45/06* (2013.01); *G06Q 30/0241* (2013.01); *G06Q 90/00* (2013.01); *A61K 2039/505* (2013.01); *A61K 2039/507* (2013.01); *A61K 2039/54* (2013.01); *A61K 2039/545* (2013.01); *A61K 2039/55* (2013.01); *C07K 2317/56* (2013.01)

(58) Field of Classification Search
CPC .. C07K 16/22; C07K 2317/56; A61K 9/1271; A61K 31/337; A61K 31/4745; A61K 31/704; A61K 39/3955; A61K 45/06; A61K 2039/505; A61K 2039/507; A61K 2039/54; A61K 2039/545; A61K 2039/55; A61P 43/00; A61P 15/08; A61P 35/00
See application file for complete search history.

(56) References Cited

U.S. PATENT DOCUMENTS

| | | |
|---|---|---|
| 6,054,297 A | 4/2000 | Carter et al. |
| 6,582,959 B2 | 6/2003 | Kim |
| 6,703,020 B1 | 3/2004 | Thorpe et al. |
| 6,884,879 B1 | 4/2005 | Baca et al. |
| 7,060,269 B1 | 6/2006 | Baca et al. |
| 7,169,901 B2 | 1/2007 | Baca et al. |
| 7,297,334 B2 | 11/2007 | Baca et al. |
| 7,365,166 B2 | 4/2008 | Baca et al. |
| 7,375,193 B2 | 5/2008 | Baca et al. |
| 7,622,115 B2 * | 11/2009 | Fyfe ................... A61K 39/3955 424/143.1 |
| 9,795,672 B2 | 10/2017 | Fyfe et al. |
| 2003/0086930 A1 | 5/2003 | Mueller et al. |
| 2003/0190317 A1 | 10/2003 | Baca et al. |
| 2003/0203409 A1 | 10/2003 | Kim |
| 2003/0206899 A1 | 11/2003 | Ferrara et al. |
| 2005/0112126 A1 | 5/2005 | Baca et al. |
| 2005/0186208 A1 | 8/2005 | Fyfe et al. |
| 2006/0013819 A1 | 1/2006 | Kelsey |
| 2006/0093601 A1 | 5/2006 | Fong et al. |
| 2007/0166388 A1 | 7/2007 | Desai |
| 2008/0299116 A1 | 12/2008 | Van Bruggen et al. |
| 2011/0206662 A1 * | 8/2011 | Dupont ................ A61K 31/282 424/133.1 |
| 2017/0100478 A1 | 4/2017 | Fyfe et al. |
| 2019/0185555 A1 | 6/2019 | Swamy et al. |

FOREIGN PATENT DOCUMENTS

| | | |
|---|---|---|
| CA | 2526085 A1 | 1/2005 |
| CA | 2286330 | 6/2008 |
| EP | 0666868 B1 | 4/2002 |
| EP | 1325932 B9 | 4/2005 |
| EP | 2481405 | 8/2012 |
| EP | 3064509 A2 | 9/2016 |
| EP | 3064509 A3 | 9/2016 |
| WO | 94/10202 | 5/1994 |
| WO | 96/30046 | 10/1996 |
| WO | 98/45331 | 10/1998 |

(Continued)

OTHER PUBLICATIONS

Wright et al., Cancer 107: 83-89 (Year: 2006).*
Rose et al., The Oncologist 10: 205-214 (Year: 2005).*
Sehouli et al., J Clin Oncology 26: 3176-3182 (Year: 2008).*
Tol et al., N Engl J Med. 5;360(6):563-72 (Year: 2009).*
Cochran et al., J. Immunol. Meth. 287: 147-158 (Year: 2004).*
Yu et al., Investigative Ophthalmology & Visual Science 49(2): 522-527 (Year: 2008).*
Bookman et al., The Oncologist 4: 87-94 (Year: 1999).*
Herzog et al., Gynecologic Oncology 90: S45-S50 (Year: 2003).*
Tsunetoh et al., Cancer biology and Therapy 10: 1137-1145 (Year: 2010).*

(Continued)

*Primary Examiner* — Phuong Huynh
(74) *Attorney, Agent, or Firm* — Grant Kalinowski

(57) ABSTRACT

This invention concerns methods of treating a patient diagnosed with a platinum-resistant ovarian cancer comprising administering to said patient an effective amount of an anti-VEGF antibody and a chemotherapeutic.

20 Claims, 3 Drawing Sheets

Specification includes a Sequence Listing.

(56) References Cited

FOREIGN PATENT DOCUMENTS

| WO | 98/45332 | 10/1998 |
|---|---|---|
| WO | 2005/000900 A1 | 1/2005 |
| WO | 2005/012359 A2 | 2/2005 |
| WO | 2005/044853 A2 | 5/2005 |
| WO | 2008/057562 A1 | 5/2008 |
| WO | 2008/075330 | 6/2008 |
| WO | 2008/094969 A2 | 8/2008 |
| WO | 2009/149150 | 12/2009 |
| WO | 2011/106300 A2 | 9/2011 |
| WO | 2011/106300 A3 | 9/2011 |
| WO | 2013/135602 | 9/2013 |
| WO | 2013/135602 A3 | 9/2013 |

OTHER PUBLICATIONS

Hurt et al., Gynecologic Oncology 115: 396-400 (Year: 2009).*
Kudoh et al., Gynecologic Oncology 122: 233-237 (Year: 2011).*
Markman et al., The Oncologist 5: 26-35 (Year: 2000).*
Ahmed et al., "Getting to Know Ovarian Cancer Ascites: Opportunities for Targeted Therapy-Based Translational Research" Frontiers in Oncology 3(256):1-12 ( 2013).
Aghajanian et al., "Efficacy in patient subgroups in OCEANS, a randomized, double-blinded, placebo-controlled, phase 3 trial of chemotherapy + bevacizumab in patients with platinum-sensitive recurrent epithelial ovarian (OC), primary peritoneal (PPC), or fallopian tube cancer (FTC)" Abstract European Society for Medical Oncology 36th Congress—ECCO 16 and ESMO 36 | ESMO, pp. 5 (5LBA) (Sep. 2011).
Aghajanian et al., "Efficacy in patient subgroups, in OCEANS,a randomized double-blinded, placebo-controlled, phase 3 trial of chemotherapy + bevacizumab in patients with platinum-sensitive recurrent epithelial ovarian, primary peritoneal, or fallopian tube cancer" Slides European Society for Medical Oncology 36th Congress—ECCO 16 and ESMO 36 | ESMO, (Sep. 2011).
Aghajanian et al., "OCEANS: A randomized, double-blinded, placebo-controlled, phase III trial of chemotherapy with or without bevacizumab (BEV) in patients with platinum-sensitive recurrent epithelial ovarian (EOC), primary peritoneal (PPC), or fallopian tube cancer (FTC)" J Clin Oncol (Abstract LBA5007; Presented Saturday, Jun. 4, 2011 ASCO Annual Meeting), 29(Suppl):1-2 (2011) https://meetinglibrary.asco.org/record/61994/abstract.
"Avastin (bevacizumab) Product Label":1-25 (Jul. 2009).
"Avastin Product Monograph":1-94 (Feb. 23, 2017).
Avastin Summary of Product Characeristics (SmPC), pp. 1-44 (2008).
Bidus et al. et al., "Sustained response to bevacizumab in refractory well-differentiated ovarian neoplasms" Gynecol Oncol 102(1):5-7 ( 2006).
Biganzoli, L., "State of the art therapy for HER2-negative metastatic breast cancer" EJC Supplements 6:10-15 (2008).
Burger et al., "Phase II trial of bevacizumab in persistent or recurrent epithelial ovarian cancer (EOC) or primary peritoneal cancer (PPC): a Gynecologic Oncology Group (GOG) study" Journal of Clinical Oncology (abstract 5009), 23(16S Jun. 1):1 (2005).
Burger, R., "Experience With Bevacizumab in the Management of Epithelial Ovarian Cancer" J Clin Oncol 25(20):2902-2908 (Jul. 10, 2007).
Burger, R., "Role of vascular endothelial growth factor inhibitors in the treatment of gynecologic malignancies" J Gynecol Oncol 21(1):3-11 (Mar. 2010).
Campos et al., "Safety of maintenance bevacizumab after first-line chemotherapy for advanced ovarian and mullerian cancers" J Clin Oncol (2007 ASCO Annual Meeting Proceedings (Post-Meeting Edition) Abstract 5517), 25(18S Suppl Jun. 20):5517 (2007).
Cohn et al. et al., "Bevacizumab and weekly taxane chemotherapy demonstrates activity in refractory ovarian cancer" Gynecol Oncol 102(2):134-139 (Aug. 2006).

Coleman et al., "A phase III randomized controlled clinical trial of carboplatin and paclitaxel alone or in combination with bevacizumab followed by bevacizumab and secondary cytoreductive surgery in platinum-sensitive, recurrent ovarian, peritoneal primary and fallopian tube cancer (Gynecologic Oncology Group 0213)" Gynecologic Oncology (3—Scientific Plenary), 137:3-4 (2015).
Cristea et al., "Practical considerations in ovarian cancer chemotherapy" Ther Adv Med Oncol 2(3):175-187 (May 2010).
Diaz et al., "The safety and efficacy of bevacizumab therapy in recurrent ovarian carcinoma" J Clin Oncol (2008 ASCO Meeting Proceedings (Post-Meeting Edition) Abstract 16528), 26(15S Suppl May 20):16528 ( 2008).
F. Hoffmann-La Roche Ltd., "Third phase III study of Avastin-based regimen met primary endpoint in ovarian cancer" (accessed Jun. 15, 2017),:1-8 (Feb. 8, 2011) http://www.roche.com/media/store/releases/med-cor-2011-02-08.htm.
Friberg et al., "Bevacizumab (B) plus erlotinib (E) for patients (pts) with recurrent ovarian (OC) and fallopian tube (FT) cancer: Preliminary results of a multi-center phase II trial" J Clin Oncol (Abstract 5018), 24(18S Part I of II):260s (Jun. 20, 2006).
Genentech, "A Phase III, Multicenter, Randomized, Blinded, Placebo-Controlled Trial of Carboplatin and Gemcitabine Plus Bevacizumab in Patients With Platinum-Sensitive Recurrent Ovary, Primary Peritoneal, or Fallopian Tube Carcinoma" (ClinicalTrials Identifier: NCT00434642; accessed Jun. 15, 2017),:1-3 (Apr. 25, 2009) https://clinicaltrials.gov/archive/NCT00434642/2009_04_25.
Genentech, "A Study of Carboplatin and Gemcitabine Plus Bevacizumab in Patients With Ovary, Peritoneal, or Fallopian Tube Carcinoma (OCEANS)" (ClinicalTrials.gov Identifier: NCT00434642; First Received: Feb. 9, 2007; Last Updated: Aug. 22, 2008; ClinicalTrials.gov processed this record on Oct. 9, 2008; Internet Archive Wayback Machine Oct. 10, 2008-Jul. 5, 2016),:1-4 http://clinicaltrials.gov/ct2/show/NCT00434642.
Genentech, "Genentech Pipeline: The Phases of Clinical Trials" (Internet Archive Wayback Machine Jan. 13, 2008-Jan. 18, 2012; retrieved Aug. 31, 2016),:1 https://web.archive.org/web/20090714033045/http://gene.com/gene/pipeline/trial-education/clinical-dev-phases.html.
Hoffmann-La Roche, "AURELIA: A multi-center, open-label, randomised, two-arm phase III trial of the effect on progression free survival of bevacizumab plus chemotherapy versus chemotherapy alone in patients with platinum-resistant, epithelial ovarian, fallopian tube or primary peritoneal cancer" (ClinicalTrials.gov, ClinicalTrials Identifier: NCT00976911, accessed Aug. 9, 2017),:1-3 (Mar. 15, 2011) https://clinicaltrials.gov/archive/NCT00976911/2011_03_15.
Jahanzeb et al., "Novel Therapeutic Directions for Patients With Advanced Breast Cancer" (retrieved Mar. 7, 2017),:1-5 (Jan. 31, 2007) http://www.medscape.org/viewarticle/551402_print.
Kouta et al., "The role of bevacizumab in combination with pegylated liposomal doxorubicin in patients with platinum-resistant recurrent or refractory ovarian cancers" Journal of Clinical Oncology 29(15 suppl.):5018 (May 2011).
Ledermann et al., "Clinical trials and decision-making strategies for optimal treatment of relapsed ovarian cancer" Eur J Cancer 47( Suppl 3):S104-S115 (Sep. 2011).
Lortholary et al., "Weekly paclitaxel as a single agent or in combination with carboplatin or weekly topotecan in patients with resistant ovarian cancer: the CARTAXHY randomized phase II trial from Groupe d'Investigateurs Nationaux pour l'Etude des Cancers Ovariens (GINECO)" Annals of Oncology 23:346-352 ( 2012).
Miller et al., "A Randomized phase III trial of paclitaxel plus bevacizumab as first-line therapy for locally recurrent or metastatic breast cancer : a trial coordinated by the Eastern Cooperative Oncology Group (E2100)" Breast Can Res Treat (Abstract 3), 94( Suppl 1):S6 ( 2005).
Miller et al., "Capecitabine plus bevacizumab in first line metastatic breast cancer: an interim safety and efficacy report of the first phase of xeloda plus avastin 1st line metastatic breast cancer trial" Breast Cancer Research and Treatment (Abstract 2068), 100( Suppl 1):S103 (Dec. 2006).

(56) References Cited

OTHER PUBLICATIONS

Miller et al., "Randomized Phase III Trial of Capecitabine Compared with Bevacizumab Plus Capecitabine in Patients with Previously Treated Metastatic Breast Cancer" Journal of Clinical Oncology 23(4):792-799 ( 2005).
Monk et al. et al., "Activity of bevacizumab (rhuMAB VEGF) in advanced refractory epithelial ovarian cancer" Gynecol Oncol 96(3):902-905 ( 2005).
Monk et al., "Changing the paradigm in the treatment of platinum-sensitive recurrent ovarian cancer: from platinum doublets to nonplatinum doublets and adding antiangiogenesis compounds" Int J Gynecol Cancer 19(S2):S63-S67 (Dec. 2009).
National Cancer Institute, "A Phase III Trial of Carboplatin and Paclitaxel Plus Placebo Versus Carboplatin and Paclitaxel Plus Concurrent Bevacizumab (NSC # 704865, IND #7921) Followed By Placebo, Versus Carboplatin and Paclitaxel Plus Concurrent and Extended Bevacizumab, in Women With Newly Diagnosed, Previously Untreated, Suboptimal Advanced Stage Epithelial Ovarian, Primary Peritoneal, or Fallopian Tube Cancer" (NCT00262847; accessed Jun. 26, 2017,:1-7 (Oct. 13, 2009).
National Cancer Institute, "A Phase III Randomized Controlled Clinical Trial of Carboplatin and Paclitaxel Alone or in Combination With Bevacizumab (NSC #704865, IND #7921) Followed by Bevacizumab and Secondary Cytoreduction Surgery in Platinum-Sensitive, Recurrent Ovarian, Peritoneal Primary and Fallopian Tube Cancer" (NCT00565851, accessed Jun. 15, 2017),:1-6 (Feb. 22, 2010) https://clinicaltrials.gov/archive/NCT00565851/2010_02_22.
National Comprehensive Cancer Network (NCCN), "Clinical Practice Guidelines in Oncology: Ovarian Cancer" (V.I.2008),:1-39 ( 2008) http://www.nccn.org/professionals/physician_gls/PDF/ovarian.pdf.
O'Shaughnessy et al., "RiBBON 1 and RiBBON 2: Phase III Trials of Bevacizumab with Standard Chemotherapy for Metastatic Breast Cancer" Clinical Breast Cancer 8(4):370-373 ( 2008).
Perren et al., "ICON7: A Phase III Randomised Gynaecologic Cancer Intergroup Trial of Concurrent Bevacizumab and Chemotherapy Followed By Maintenance Bevacizumab, versus Chemotherapy Alone in Women with Newly Diagnosed Epithelial Ovarian (EOC), Primary Peritoneal (PPC) or Fallopian Tube Cancer (FTC)" Annals of Oncology (Abstract LBA4), 21( Suppl 8):viii2-viii3 (Oct. 2010).
Pujade-Lauraine et al., "AURELIA: A randomized phase III trial evaluating bevacizumab (BEV) plus chemotherapy (CT) for platinum (PT)-resistant recurrent ovarian cancer (OC)" J Clin Oncol (Abstract LBA5002), 30(18 Suppl):1-2 ( 2012) http://ascopubs.org/doi/abs/10.1200/jco.2012.30.18_suppl.lba5002.
Pujade-Lauraine et al., "AURELIA: A randomized phase III trial evaluating bevacizumab combined with chemotherapy for platinum-resistant recurrent ovarian cancer" (Slides presented at the Jun. 2012 ASCO Annual Meeting),:1-17 (Jun. 2012).
Richardson et al., "Does repeat usage of bevacizumab in patients with progressive recurrent ovarian cancer offer a survival advantage?" J Clin Oncol (2009 ASCO Annual Meeting Proceedings (Post-Meeting Edition) Abstract e16510), 27(15S Suppl May 20):e16510 ( 2009).
Robert et al., "RIBBON-1: Randomized, double-blind, placebo-controlled, phase III trial of chemotherapy with or without bevacizumab (B) for first-line treatment of HER2-negative locally recurrent or metastatic breast cancer (MBC)" J Clin Oncol (Abstract 1005), 27(15S, Part I of II):42s (May 20, 2009).
Roche, Avastin phase III study shows positive results in women with advanced ovarian cancer; Retrieved Jun. 15, 2017, pp. 1-7 (Investor Update Feb. 25, 2010) http://www.roche.com/investors/updates/inv-update-2010-02-25.htm.
Roche, "Roche study showed that adding Avastin to chemotherapy cut the risk of the disease getting worse in difficult-to-treat recurrent ovarian cancer by half: First phase III study of Avastin plus chemotherapy in platinum-resistant ovarian cancer" (Media Release retrieved Jun. 15, 2017),:1-7 (Jun. 2, 2012) http://www.roche.com/media/store/releases/med-cor-2012-06-02.htm.
Roche: Avastin phase III study shows positive results in women with advanced ovarian cancer; Retrieved from the Internet: URL:http://www.roche.com/media/media_releases/med-cor-2010-02-25.htm, pp. 1-4 (Media Release Feb. 25, 2010).
Roche: Third phase III study of Avastin-based regimen met primary endpoint in ovarian cancer; Retrieved from the Internet: URL:http://www.roche.com/media/media_releases/med-cor-2011-02-08.htm, pp. 1-5 (Media Release Feb. 8, 2011).
Sledge et al., "Safety and efficacy of capecitabine (C) plus bevacizumab (B) as first-line in metastatic breast cancer" J Clin Oncol (Abstract 1013), 25(18S):1013 (Jun. 20, 2007).
Teoh et al., "Antiangiogenic therapies in epithelial ovarian cancer" Cancer Control 18(1):31-43 (Jan. 2011).
U.S. Appl. No. 61/307,095, pp. 78 (filed Feb. 23, 2010).
U.S. Appl. No. 61/351,231, pp. 88 (filed Jun. 3, 2010).
U.S. Appl. No. 61/360,059, pp. 99 (filed Jun. 30, 2010).
U.S. Appl. No. 61/439,819, pp. 109 (filed Feb. 4, 2011).
Varughese et al., "Trial Design Strategies for Vascular-Targeted Therapy of Patients with Ovarian Cancer" Clinical Ovarian Cancer 2(1):24-30 (May 2009).
Wright et al., "A multi-institutional evaluation of factors predictive of toxicity and efficacy of bevacizumab for recurrent ovarian cancer" Int J Gynecol Cancer 18:400-406 ( 2008).
Hamilton et al., "Intraperitoneal bevacizumab for the palliation of malignant ascites in refractory ovarian cancer" Gynecologic Oncology(111):530-532 ( 2008).
Yanjun, Cai, Master Theses Experimental Study on the Inhibitory Effect of anti-VEGF Monocoly Antibody Bevacizumab and DDP to Nude Mice Ascites which is Inducted by High Level VEGF expression Ovarian Cancer Cell Lines. First Military Medical University (now named Southern Medical University). Partial translation to English ( May 15, 2007).
Yanjun, Cai, Master Theses Experimental Study on the Inhibitory Effect of anti-VEGF Monocoly Antibody Bevacizumab and DDP to Nude Mice Ascites which is Inducted by High Level VEGF expression Ovarian Cancer Cell Lines. First Military Medical University (now named Southern Medical University. (Chinese language version) ( May 5, 2007).
U.S. Appl. No. 60/991,302, filed Nov. 30, 2007, Fuh et al.
"Current Clinical Trials of the Anti-VEGF Monoclonal Antibody Bevacizumab" Oncology 15(8):web pp. 1-6 (Aug. 2001).
(International Search Report for International Patent Appln. No. PCT/EP2013/054818).
(Office Action dated May 29, 2009 in U.S. Appl. No. 12/127,733).
(Office Action dated Nov. 30, 2007 in U.S. Appl. No. 11/537,281).
(Office Action dated Mar. 20, 2013 in U.S. Appl. No. 13/032,532).
(Office Action dated Apr. 3, 2015 in U.S. Appl. No. 14/157,351).
(Office Action dated Dec. 16, 2015 in U.S. Appl. No. 14/157,351).
(Written Opinion for International Patent Appln. No. PCT/EP/2013/054818).
Abstracts Presented for the Fortieth Annual Meeting of the Society of Gynecologic Oncologists; Gynecologic Oncology, Academic Press, London, GB, vol. 112, No. 2, pp. S2-S185 ( Feb. 1, 2009).
Aghajanian et al., "OCEANS: A Randomized, Double-Blind, Placebo-Controlled Phase III Trial of Chemotherapy with or without Bevacizumab in Patients with Platinum-Sensitive Recurrent Epithelial Ovarian, Primary Peritoneal, or Fallopian Tube Cancer" Journal of Clinical Oncology:1-7 (Apr. 23, 2012).
Alberts et al., "Improved therapeutic index of carboplatin plus cyclophosphamide versus cisplatin plus cyclophosphamide: Final Report by the Southwest Oncology Group of a Phase III randomized trial in stages III and IV ovarian cancer" J Clin. Oncol. 10(5):706-717 (May 1992).
Alvarez et al., "The prognostic significance of angiogenesis in epithelial ovarian carcinoma" Clin. Cancer Res. 5:587-591 (Mar. 1999).
Bamias et al., "Angiogenesis: a promising therapeutic target for ovarian cancer" Critical Reviews in Oncology/Hematology 84(3):314-326 (Dec. 2012).

(56) References Cited

OTHER PUBLICATIONS

Bast et al., "A radioimmunoassay using a monoclonal antibody to monitor the course of epithelial ovarian cancer" N Engl J Med 309(15):883-887 ( 1983).
Bast et al., "Chemotherapy: A new standard combination for recurrent ovarian cancer" Nat Rev Clin Oncol 7(10):559-560 (Oct. 2010).
Burger et al., "Phase II trial of bevacizumab in persistent or recurrent epithelial ovarian cancer or primary peritoneal cancer: a Gynecologic Oncology Group study" J clin Oncol 25(33):5165-5171 ( 2007).
Burger et al., "Phase III trial of bevacizumab (BEV) in the primary treatment of advanced epithelial ovarian cancer (EOC), primary peritoneal cancer (PPC), or fallopian tube cancer (FTC): A Gynecologic Oncology Group study" J. Clin. Oncol. (Abstract No. LBA1), 28:18s ( 2010).
Cannistra et al., "Phase II study of bevacizumab in patients with platinum resistant ovarian cancer or primary peritoneal serous cancer" J Clin Oncol 25(33):5180-5186 ( 2007).
Chura et al., "Bevacizumab plus cyclophosphamide in heavily pretreated patients with recurrent ovarian cancer" Gynecologic Oncology 107(2):326-330 (Nov. 1, 2007).
Cohen et al., "FDA drug approval summary: Bevacizumab plus FOLFOX4 as second-line treatment of colorectal cancer" The Oncologist 12(3):356-361 (Mar. 2007).
International Search Report and Written Opinion for International Patent Application No. PCT/US2011/025651.
Du Bois et al., "A randomized clinical trial of cisplatin/paclitaxel versus carboplatin/paclitaxel as first-line treatment of ovarian cancer" J Natl Cancer I 95(17):1320-1330 (Sep. 3, 2003).
Ferrara et al., "Clinical applications of angiogenic growth factors and their inhibitors" Nat Med 5(12):1359-1364 (Dec. 1999).
Folkman, "Tumor angiogenesis: Therapeutic implications" N Engl J Med 285:1182-1186 (Nov. 18, 1971).
Foster et al., "A review of the current evidence for maintenance therapy in ovarian cancer" Gynecologic Oncol. 115(2):290-301 (Nov. 1, 2009).
Fujimoto et al., "Clinical implications of expression of vascular endothelial growth factor in metastatic lesions of ovarian cancers" British Journal of Cancer 85(3):313-316 ( 2001).
Garcia et al., "Addition of bevacizumab to paclitaxel/carboplatin in first-line management of advanced ovarian cancer: Results of the GOG 0218 Phase III Study" Clin. Ovarian Cancer 3(2):E1-E5 (Nov. 2010).
Garcia et al., "Phase II Clinical Trial of Bevacizumab and Low-Dose Metronomic Oral Cyclophosphamide in Recurrent Ovarian Cancer: A Trail of the California, Chicago, and Princess Margaret Hospital Phase II Consortia" Journal of Clinical Oncology 26(1):76-82 (Jan. 1, 2008).
Gasparini et al., "Prognostic and predictive value of tumour angiogenesis in ovarian carcinomas" Int. J. Cancer (Precl. Oncol.) 69:205-211 ( 1996).
Gasparini, G., "The rationale and future potential of angiogenesis inhibitors in neoplasia" Drugs 58:17-38 ( 1999).
Gerber and Ferrara, "Pharmacology and pharmacodynamics of bevacizumab as monotherapy or in combination with cytotoxic therapy in preclinical studies" Cancer Research 65(3):671-680 (Feb. 1, 2005).
Giles, "The vascular endothelial growth factor (VEGF) signaling pathway: A therapeutic target in patients with hematologic malignancies" The Oncologist 6(5(suppl)):32-39 ( 2001).
Gonzalez et al., "Exploratory outcome analyses according to stage and residual disease in the ICON7 trial of front-line carboplatin/paclitaxel with or without bevacizumab for ovarian cancer" Poster American Society of Clinical Oncology 51st Annual Meeting, pp. 5548 ( May 30, 2015).
Guppy and Rustin, "CA125 Response: can it replace the traditional response criteria in ovarian cancer?" Oncologists 7:437-443 ( 2002).
Han and Monk, "Bevacizumab in the treatment of ovarian cancer" Expert Review of Anticancer Therapy, Future Drugs Ltd., UK 7(10):1339-1345 (Oct. 1, 2007).
Hasan et al., "VEGF antagonists" Expert Opinion Biol. Ther. 1(4):703-718 ( 2001).
Herzog et al., "Preliminary safety and efficacy results of a phase II study of oxaliplatin, docetaxel, and bevacizumab as first-line therapy of advanced cancer of the ovary, peritoneum, and fallopian tube" J. Clin. Oncol. (Abstract No. 5518), 25:18S ( 2007).
Herzog et al., "Preliminary safety results of TEACO, a phase 2 trial of oxaliplatin, docetaxel and bevacizumab as first line therapy for advanced cancer of the ovary, peritoneum and fallopian tube" Gynecologic Oncology 112(2 Suppl Abstract 48):S2-S185 ( 2009).
Hollingsworth et al., "Tumor angiogenesis in advanced stage ovarian carcinoma" Am. J. Pathol. 147(1):33-41 (Jul. 1995).
Houck et al., "The vascular endothelial growth factor family: Identification of a fourth molecular species and characterization of alternative splicing of RNA" Mol. Endocrin. 5:1806-1814 ( 1991).
Hu et al., "Vascular endothelial growth factor immunoneutralization plus paclitaxel markedly reduces tumor burden and ascites in athymic mouse model of ovarian cancer" American Journal of Pathology 161(5):1917 ( 2002).
Jemal et al., "Cancer Statistics, 2004" CA Cancer J Clin 54:8-29 ( 2004).
Kim et al., "Combined anti-angiogenic therapy against VEGF and integrin alphvBeta3 in an orthotopic model of ovarian cancer" Cancer Biology and Therapy 8(23):2261-2270 ( 2009).
Kim et al., "Inhibition of vascular endothelial growth factor-induced angiogenesis suppresses tumour growth in vivo" Nature 362:841-844 (Apr. 1993).
Klagsbrun and D'Amore, "Regulators of angiogenesis" Ann Rev Physiol 53:217-239 ( 1991).
Leung et al., "Vascular Endothelial Growth Factor is a Secreted Angiogenic Mitogen" Science 246:1306-1309 (Dec. 8, 1989).
Luo et al., "Differential inhibition of fluid accumulation and tumor growth in two mouse ascites tumors by an anti vascular endothelial growth factor/permeability factor neutralizing antibody" Cancer Res 58:2594-2600 ( 1998).
Mabuchi et al., "Maintenance treatment with bevacizumab prolongs survival in an in vivo ovarian cancer model" Clin. Cancer Res. 14(23):7781-7789 (Dec. 1, 2008).
Malonne et al., "Mechanisms of tumor angiogenesis and therapeutic implications: angiogenesis inhibitors" Clin. Exp. Metastas 17:1-14 ( 1999).
McGonigle et al., "Combined weekly topotecan and biweekly bevacizumab in women with platinum-resistant ovarian, peritoneal, or fallopian tube cancer: results of a phase 2 study" Cancer 117(16):3731-3740 (Aug. 15, 2011).
McGuire et al., "Cyclophosphamide and cisplatin compared with paclitaxel and cisplatin in patients with stage III and stage IV ovarian cancer" New Engl J Med 334:1-6 ( 1996).
McMeekin et al., "Phase II study of intravenous (IV) bevacizumab and paclitaxel, and intraperitoneal (IP) cisplatin, followed by bevacizumab consolidation for advanced ovarian (O) or peritoneal (P) cancers" J. Clin. Oncol. (Abstract No. 5540), 27:15s ( 2009).
Micha et al., "A Phase II study of outpatient first-line paclitaxel carboplatin, and bevacizumab for advanced-stage epithelial ovarian, peritoneal, and fallopian tube cancer" Int J Gynecol Cancer 17:771-776 ( 2007).
Monk et al. et al., "Salvage bevacizumab (rhuMAB VEGF)-based therapy after multiple prior cytotoxic regimens in advanced refractory epithelial ovarian cancer" Gynecol Oncol 102(2):140-4 ( 2006).
Nakanishi et al., "The expression of vascular endothelial growth factor and transforming growth factor-beta associates with angiogenesis in epithelial ovarian cancer" Int J Gynecol Pathol 16(3):256-262 (Jul. 1997).
Ohtani et al., "A case of rapidly growing ovarian squamous cell carcinoma successfully controlled by weekly paclitaxel-carboplatin administration" Gynecologic Oncology 79:515-518 ( 2000).
Oza et al., "Standard chemotherapy with or without bevacizumab for women with newly diagnosed ovarian cancer (ICON7): overall

(56) References Cited

OTHER PUBLICATIONS survival results of a phase 3 randomised trial" The Lancet Oncology (published online) (Jun. 24, 2015).
Ozols et al., "Phase III trial of carboplatin and paclitaxel compared with cisplatin and paclitaxel in patients with optimally resected stage III ovarian cancer: a gynecologic oncology group study" J Clin. Oncol. 21(17):3194-3200 (Sep. 1, 2003).
Paley et al., "Vascular endothelial growth factor expression in early stage ovarian carcinoma" Cancer 80( Suppl 98-106) ( 1997).
Penson et al., "Phase II study of carboplatin, paclitaxel, and bevacizumab with maintenance bevacizumab as first-line chemotherapy for advanced mullerian tumors" J. Clin. Oncol. 28(1):154-159 (Jan. 1, 2010).
Perren et al., "A Phase 3 Trial of Bevacizumab in Ovarian Cancer" The New England Journal of Medicine 365:2484-96 ( 2011).
Pfisterer et al., "Gemcitabine plus carboplatin compared with carboplatin in patients with platinum-sensitive recurrent ovarian cancer: an intergroup trial of the AGO-OVAR, the NCIC CTG, and the EORTC GCG" J. Clin. Oncol. 24:4699-4707 ( 2006).
Piccart et al., "Randomized intergroup trial of cisplatin-paclitaxel versus cisplatin-cyclophosphamide in women with advanced epithelial ovarian cancer: Three-Year Results" J Natl. Cancer I 92(9):699-708 (May 3, 2000).
Pietzner et al., "Long Term Combination Treatment with Bevacizumab, Pegylated Liposomal Doxorubicin and Regional Abdominal Hyperthermia in Platinum Refractory Ovarian Cancer: A Case Report and Review of the Literature" Anticancer Research 31(8):2675-2677 ( 2011).
Popkov et al., "Human/mouse cross-reactive anti-VEGF receptor 2 recombinant antibodies selected from an immune b9 allotype rabbit antibody library" J Immunol Methods 288:149-164 (May 2004).
Poveda et al., "Management of recurrent ovarian cancer with systemic therapy" EJC Supplements 5(1):29-36 ( 2007).
Presta et al., "Humanization of an Anti-Vascular Endothelial Growth Factor Monoclonal Antibody for the Therapy of Solid Tumors and Other Disorders" Cancer Res 57(20):4593-4599 (Oct. 15, 1997).
Reis-Filho and Tutt, "Triple negative tumours: a critical review" Histopathology 52:108-118 (Jan. 2008).
Richardson et al., "Combination gemcitabine, platinum, and bevacizumab for the treatment of recurrent ovarian cancer" Gynecologic Oncol., Academic Press 111(3):461-466 (Dec. 1, 2008).
Roche: Avastin phase III study shows positive results in women with advanced ovarian cancer; Retrieved from the Internet: URL:http://www.roche.com/media/media_releases/med-cor-2010-02-25.htm.
Roche: Second phase III study showed Avastin-containing regimen helped women with ovarian cancer live longer without their disease getting worse: Retrieved from the Internet: URL:http://www.roche.com/med-cor-2010-07-02.
Roche: Third phase III study of Avastin-based regimen met primary endpoint in ovarian cancer; Retrieved from the Internet: URL:http://www.roche.com/media/media_releases/med-cor-2011-02-08.htm.
Rose et al., "Preliminary results of a phase II study of oxaliplatin, docetaxel, and bevacizumab as first-line therapy of advanced cancer of the ovary, peritoneum, and fallopian tube" J. Clin. Oncol. (Abstract No. 5546), 27:15s ( 2009).
Rustin et al., "Re: new guidelines to evaluate the response to treatment in solid tumors (ovarian cancer)" J Natl. Cancer I 96(6):487-488 (Mar. 17, 2004).
Rustin et al., "Use of CA-125 in clinical trial evaluation of new therapeutic drugs for ovarian cancer" Clin. Cancer Res. 10:3919-3926 (Jun. 1, 2004).
Rustin et al., "Use of CA-125 to define progression of ovarian cancer in patients with persistently elevated levels" J Clin. Oncol. 19(20):4054-4057 (Oct. 15, 2001).
Rustin, G., "Use of CA-125 to assess response to new agents in ovarian cancer trials" J. Clin. Oncol. 21(10s Suppl May 15 Supplement):187x-193x ( 2003).
Sato, "Molecular diagnosis of tumor angiogenesis and anti-angiogenic cancer therapy" Int J Clin Oncol 8(4):200-206 (Aug. 2003).
Sugiyama "Second-Line Treatment Using Novel Chemotherapeutic and Biologic Agents" Japanese Journal of Cancer and Chemotherapy 36:730-735 (May 2009).
Streit et al., "Angiogenesis, lymphangiogenesis, and melanoma metastasis" Oncogene 22(20):3172-3179 (May 19, 2003).
Stuart et al., "2010 Gynecologic Cancer InterGroup (GCIG) Consensus Statement on Clinical Trails in Ovarian Cancer" Int J of Gynecol Cancer 21(4):750-755 (May 2011).
Swenerton et al., "Cisplatin-cyclophosphamide versus carboplatin-cyclophosphamide in advanced ovarian cancer: a randomized phase III study of the National Cancer Institute of Canada Clinical Trials Group" J Clin. Oncol. 10(5):718-726 (May 1992).
Therasse et al., "New guidelines to evaluate the response to treatment in solid tumors" J Natl Cancer Institute 92(3):205-216 ( 2000).
Tonini et al., "Molecular basis of angiogenesis and cancer" Oncogene 22(42):6549-6556 (Sep. 29, 2003).
Tsunetoh et al., "Topotecan as a molecular targeting agent which blocks the Akt and VEGF cascade in platinum-resistant ovarian cancers" Cancer Biology & Therapy 10(11):1137-1146 (Dec. 1, 2010).
Van Hinsbergh et al., "Angiogenesis and anti-angiogenesis: perspectives for the treatment of solid tumors" Ann Oncol 4( Suppl 4):60-63 ( 1999).
Wright, "Bevacizumab combination therapy in recurrent, platinum-refractory, epithelial ovarian carcinoma: A retrospective analysis" Cancer 107(1):83-89 (Jul. 1, 2006).
Yamamoto et al., "Expression of vascular endothelial growth factor (VEGF) in epithelial ovarian neoplasms: correlation with clinic pathology and patient survival, and analysis of serum VEGF levels" Br J Cancer 76:1221-1227 ( 1997).
Yoneda et al., "Expression of angiogenesis-related genes and progression of human ovarian carcinomas in nude mice" J Natl Cancer I 90(6):447-454 (Mar. 18, 1998).
Aghajanian et al., "Final overall survival and safety analysis of OCEANS, a phase 3 trial of chemotherapy with or without bevacizumab in patients with platinum-sensitive recurrent ovarian cancer" Gynecologic Oncology 139:10-16 ( 2015).
Aghajanian et al., "OCEANS: A randomized, double-blind, placebo-controlled Phase III trial of chemotherapy with or without bevacizumab in patients with platinum-sensitive recurrent epithelial ovarian, primary peritoneal, or fallopian tube cancer" Journal of Clinical Oncology 30(17):2039 (Jun. 10, 2012).
Anonymous, "A Study of Carboplatin and Gemcitabine Plus Bevacizumab in Patients with Ovary, Peritoneal, or Fallopian Tube Carcinoma—Study Results—ClinicalTrial.gov Retrieved from the Internet: URL:https://clinicaltrials.gov/cts/show/results/NCT00434642?SECT=x30125&view-results#evnt" (Jun. 1, 2016).
Tomao et al., "Improvement in Progression-Free Survival in OCEANS Bevacizumab Arm: A Critical Point of View" Journal of Clinical Oncology 31(1):166-167 ( 2012).
Ozols, "Challenges for chemotherapy in ovarian cancer" Annals of Oncology 17(5):v181-v187 ( 2006).
Armstrong et al., "Intraperitoneal cisplatin and paclitaxel in ovarian cancer" New England Journal of Medicine 354(1):34-43 ( 2006).
Bookman, "Developmental Chemotherapy and Management of Recurrent Ovarian Cancer" Journal of Clinical Oncology 21(10):149s-167s ( 2003).
Bray et al., "Ovarian cancer in Europe: Cross-sectional trends in incidence and mortality in 28 countries, 1953-2000" Int J Cancer 113:977-990 ( 2005).
Chan et al., "Patterns and progress in ovarian cancer over 14 years" Obstetrics & Gynecology 108(3, Part 1):521-528 ( 2006).
Engel et al., "Moderate progress for ovarian cancer in the last 20 years: prolongation of survival, but no improvement in the cure rate" European Journal of Cancer 38:2435-2445 ( 2002).
Harries et al., "Part 1: Chemotherapy for epithelial ovarian cancer—treatment at first diagnosis" The Lancet Oncology 3:529-536 ( 2002).
Int'l Collaborative Ovarian Neoplasm (ICON) Group, "Paclitaxel plus carboplatin versus standard chemotherapy with either single-agent carboplatin or cyclophosphamide, doxorubicin, and cisplatin in women with ovarian cancer: the ICON3 randomised trial" The Lancet 360:505-515 ( 2002).

(56) References Cited

OTHER PUBLICATIONS

Muggia et al., "Phase III randomized study of cisplatin versus paclitaxel versus cisplatin and paclitaxel in patients with suboptimal stage III or IV ovarian cancer: a gynecologic oncology group study" Journal of Clinical Oncology 18(1):106-115 ( 2000).
NCCN, "http://www.nccn.org/professionals/physician_gls/PDF/ovarian.pdf" NCCN, Clinical Practice Guidelines in Oncology: Ovarian Cancer 1 ( 2008).
O'Malley et al., "Addition of bevacizumab to weekly paclitaxel significantly improves progression-free survival in heavily pre-treated recurrent epithelial ovarian cancer" Gynecologic Oncology 121:269-272 ( 2011).
Avastin Summary of Product Characteristics (SmPC),:1-73 ( 2017).
Biospace, "Genentech Fighting to Delay Amgen's Avastin Biosimilar":1 page (Feb. 17, 2017).
Burger et al., "Incorporation of bevacizumab in the primary treatment of ovarian cancer" N Engl J Med 365(26):2473-2483 (Dec. 29, 2011).
"Expert Report of Dr. Paul A. DiSilvestro M.D." (*Pfizer Limited* vs. *F. Hoffmann-La Roche AG and Roche Products Limited*, High Court of Justice Business and Property Courts of England and Wales Intellectual Property (ChD) Patents Court, Claim No: HP-2017-000064, executed Jun. 15, 2018),:53 pages (Jun. 15, 2018).
"First Expert Report of Dr. Paul A. DiSilvestro M.D. with CV" (*Pfizer PFE B.V.* vs. *F. Hoffmann-La Roche AG and Roche Nederland B.V.*, District Court the Hague, case No. C/09/555983, executed Jul. 16, 2018),:83 pages (Jul. 13, 2018).
Google search results regarding Pujade-Lauraine et al.,:3 pages.
Kikuchi et al., "Effects of weekly bevacizumab and pegylated liposomal doxorubicin in heavily pretreated patients with recurrent or progressed ovarian cancer" Journal of Clinical Oncology (Abstract 5547; accessed Sep. 11, 2017), 27(15S):2 pages (May 2009) http://ascopubs.org/doi/abs/10.1200/jco.2009.27.15s.5547.
Mills, G., "The State of the Fight: Ovarian Cancer" (Stand Up to Cancer website; retrieved Jul. 3, 2018),:3 pages https://web.archive.org/web/20140927002902/http://www.standup2cancer.org:80/article_archive/view/the_state_of_the_fight_ovarian_cancer.
Oza et al., "Standard chemotherapy with or without bevacizumab for women with newly diagnosed ovarian cancer (ICON7): overall survival results of a phase 3 randomised trial" Lancet Oncology 16(8):928-936 (Aug. 2015).
PCT International Preliminary Report on Patentability for F. Hoffmann-La Roche AG PCT/EP2013/054818,:10 pages (dated Sep. 16, 2014).
Reidy et al., "Bevacizumab 5 mg/kg can be infused safely over 10 minutes" J Clin Oncol 25(19):2691-2695 (Jul. 1, 2007).
Saad et al., "Progression-free survival and time to progression as primary end points in advanced breast cancer: often used, sometimes loosely defined" Annals of Oncology 20(3):460-464 (Mar. 2009).
Society of Gynecologic Oncology (SGO), "GOG 218 Phase III Trial Study Results" (retrieved Mar. 20, 2018),:1 page (Jun. 2010) https://www.sgo.org/newsroom/position-statements-2/gog-218-phase-iii-trial-study-results/.
UW Medicine, Department of Radiation Oncology, University of Washington, "Gynecologic Cancers" (retrieved Mar. 20, 2018),:7 pages https://radiationoncology.uw.edu/radiation-treatment/cancer-types/gynecologic-cancers/.
Vasey et al., "Phase III randomized trial of docetaxel-carboplatin versus paclitaxel-carboplatin as first-line chemotherapy for ovarian carcinoma" J Natl Cancer Inst 96(22):1682-1691 (Nov. 17, 2004).
Vogelzang et al., "Clinical cancer advances 2011: Annual Report on Progress Against Cancer from the American Society of Clinical Oncology" Journal of Clinical Oncology 30(1):88-109 (Jan. 1, 2012).
"A Phase III, Multicenter, Randomized, Blinded, Placebo-Controlled Trial of Carboplatin and Gemcitabine Plus Bevacizumab in Patients with Platinum-Sensitive Recurrent Ovary, Primary Peritoneal, or Fallopian Tube Carcinoma" (Protocol Synopsis; Protocol No. AVF4095g; Date Final: Nov. 21, 2006; Dates Amended: May 22, 2007 and Apr. 8, 2008),:48-53.
AbuShahin et al., "Role of gemcitabine in the treatment of ovarian cancer" Women's Health 3(3):279-290 (May 2007).
Armstrong, D., "Relapsed ovarian cancer: challenges and management strategies for a chronic disease" The Oncologist 7( Suppl 5):20-28 ( 2002).
Booth et al., "Oncology's trials" Nat Rev Drug Discov 2(8):609-610 (Aug. 2003).
Dancey and Chen, "Strategies for optimizing combinations of molecularly targeted anticancer agents" Nat Rev Drug Discov 5(8):649-659 (Aug. 2006).
Gerber et al., "Mice expressing a humanized form of VEGF-A may provide insights into the safety and efficacy of anti-VEGF antibodies" PNAS 104(9):3478-3483 (Feb. 27, 2007).
Gutman et al., "Progression-Free Survival: What Does It Mean for Psychological Well-Being or Quality of Life?" (AHRQ Publication No. 13-EHC074-EF),:74 pages (Apr. 2013).
Kola et al., "Can the pharmaceutical industry reduce attrition rates?" Nat Rev Drug Discov 3(8):711-715 (Aug. 2004).
Markman, M., et al., "Second-Line Treatment of Ovarian Cancer" Oncologist 5(1):26-35 (Jan. 1, 2000).
Nimeiri et al., "Efficacy and safety of bevacizumab plus erlotinib for patients with recurrent ovarian, primary peritoneal, and fallopian tube cancer: a trial of the Chicago, PMH, and California Phase II Consortia" Gynecol Oncol 110(1):49-55 (Jul. 2008).
O'Malley, D., "Declaration of David O'Malley, M.D." (EP Patent Application No. 16159080.7; Proprietor: F. Hoffmann-La Roche AG),:59 pages (May 16, 2019).
O'Malley, David, "Declaration of David O'Malley, M.":1-25 (Aug. 26, 2019).
Phan, S., "Declaration of See-Chun Phan, M.D." (*Holger Glas et al.* vs. *F. Hoffmann-La Roche AG*; Opposition to European Patent No. EP 2,752,189 B1),:20 pages (Apr. 12, 2018).
Poveda, Andres M., et al., "Bevacizumab Combined With Weekly Paclitaxel, Pegylated Liposomal Doxorubicin, or Topotecan in Platinum-Resistant Recurrent Ovarian Cancer: Analysis by Chemotherapy Cohort of the Randomized Phase III AURELIA Trial" J Clin Oncol 33:1-3 (Aug. 17, 2015).
Ratain et al., "Testing the wrong hypothesis in phase II oncology trials: there is a better alternative" Clin Cancer Res 13(3):781-782 (Feb. 1, 2007).
Sehouli, J., et al., "Nonplatinum Topotecan Combinations Versus Topotecan Alone for Recurrent Ovarian Cancer: Results of a Phase III Study of the North-Eastern German Society of Gynecological Oncology Ovarian Cancer Study Group" J Clin Oncol 26(19):3176-3182 (Jul. 1, 2008).
Stone et al., "Improving the design of phase II trials of cytostatic anticancer agents" Contemp Clin Trials 28(2):138-145 (Feb. 2007).
Thomas et al., Clinical Development Success Rates 2006-2015 (BIO, Biotechnology Innovation Organization),:28 pages ( 2016).
Vickers et al., "Setting the bar in phase II trials: the use of historical data for determining 'go/no go' decision for definitive phase III testing" Clin Cancer Res 13(3):972-976 (Feb. 1, 2007).
Wong, Chi Heem et al., "Estimation of clinical trial success rates and related parameters" Biostatistics 20(2):273-286 (Jan. 31, 2018).
Yang JC, et al. et al., "A randomized trial of Bevacizumab, an anti-vascular endothelial growth factor antibody, for metastatic renal cancer" New Engl J Med 349(5):427-434 (Jul. 31, 2003).
Zia et al., "Comparison of outcomes of phase II studies and subsequent randomized control studies using identical chemotherapeutic regimens" J Clin Oncol 23(28):6982-6991 (Oct. 1, 2005).

\* cited by examiner a. Choice of paclitaxel, topotecan or PLD (Caeytx)
b. 15 mg/kg q3w will be used instead if topotecan is selected and administered at a dose of 1.25 mg/m2 on a 1-5/q3w schedule
c. Refer to section 6.1.3 Treatment at disease progression only

```
SEQUENCE LISTING

<160> NUMBER OF SEQ ID NOS: 2

<210> SEQ ID NO 1
<211> LENGTH: 108
<212> TYPE: PRT
<213> ORGANISM: Artificial sequence
<220> FEATURE:
<223> OTHER INFORMATION: amino acid sequence of humanized antibody
      variable light chain

<400> SEQUENCE: 1

Asp Ile Gln Met Thr Gln Ser Pro Ser Ser Leu Ser Ala Ser Val
 1               5                  10                  15

Gly Asp Arg Val Thr Ile Thr Cys Ser Ala Ser Gln Asp Ile Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105

Ile Lys Arg

<210> SEQ ID NO 2
<211> LENGTH: 123
<212> TYPE: PRT
<213> ORGANISM: Artificial sequence
<220> FEATURE:
<223> OTHER INFORMATION: amino acid sequence of humanized antibody
      variable heavy chain

<400> SEQUENCE: 2

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Asn Tyr Gly Met Asn Trp Val Arg Gln Ala Pro Gly Lys Gly Leu
                35                  40                  45

Glu Trp Val Gly Trp Ile Asn Thr Tyr Thr Gly Glu Pro Thr Tyr
                50                  55                  60

Ala Ala Asp Phe Lys Arg Arg Phe Thr Phe Ser Leu Asp Thr Ser
                65                  70                  75

Lys Ser Thr Ala Tyr Leu Gln Met Asn Ser Leu Arg Ala Glu Asp
                80                  85                  90

Thr Ala Val Tyr Tyr Cys Ala Lys Tyr Pro His Tyr Tyr Gly Ser
                95                 100                 105
```

```
Ser His Trp Tyr Phe Asp Val Trp Gly Gln Gly Thr Leu Val Thr
                110                 115                 120
Val Ser Ser
```

COMBINATION THERAPY FOR THE TREATMENT OF OVARIAN CANCER

RELATED APPLICATIONS

This application is a continuation of U.S. application Ser. No. 14/384,863, filed Sep. 12, 2014 (now abandoned), which is a 371 of International Application No. PCT/EP2013/054818, filed Mar. 11, 2013, claiming benefit of U.S. Provisional Application No. 61/653,598, filed May 31, 2012, U.S. Provisional Application No. 61/610,128, filed Mar. 13, 2012, and U.S. Provisional Application No. 61/672,987 filed Jul. 18, 2012, the contents of each of which are incorporated herein by reference.

SEQUENCE LISTING

The instant application contains a Sequence Listing which has been submitted in ASCII format via EFS-Web and is hereby incorporated by reference in its entirety. Said ASCII copy, created on May 11, 2016 is named Sequence_listing.txt and is 2,633 bytes in size.

FIELD OF THE INVENTION

This invention concerns in general treatment of diseases and pathological conditions with anti-VEGF antibodies. More specifically, the invention concerns the treatment of human patients susceptible to or diagnosed with ovarian cancer using an anti-VEGF antibody, in combination with one or more additional anti-tumor therapeutic agents.

BACKGROUND

Epithelial ovarian cancer, along with primary peritoneal carcinoma and fallopian tube carcinoma, is the fifth most common cause of cancer-related death in women in the Europe.1 It is also the gynaecological malignancy with the highest mortality rate (Bray F et al. *Ovarian cancer in Europe: Cross-sectional trends in incidence and mortality in 28 countries,* 1953-2000. Int J Cancer 113, 977-90 (2005); National Comprehensive Cancer Network, *Clinical Practice Guidelines in Oncology:* Ovarian cancer v.1 (2008) http://www.nccn.org/professionals/physician_gls/PDF/ovarian.pdf. (2008)). Despite improvements in the treatment of ovarian cancer, increases in OS have been modest (Chan, J. K. et al. *Patterns and progress in ovarian cancer over 14 years,* Obstet. Gynecol. 108, 521-528 (2006); Engel, J. et al. *Moderate progress for ovarian cancer in the last 20 years: prolongation of survival, but no improvement in the cure rate,* Eur. J Cancer 38, 2435-2445 (2002)), and as such, mortality remains high. This is partly due to the fact that ovarian cancer is frequently not diagnosed until it has progressed to an advanced stage. Ovarian cancer is considered a chemo-responsive neoplasm, with initial response rates to systemic chemotherapy exceeding 80% when integrated with primary cytoreductive surgery (Bookman, M. A. *Developmental chemotherapy and management of recurrent ovarian cancer.* J. Clin. Oncol. 21, 149s-167s (2003)). Despite this, over 50% of women diagnosed with epithelial ovarian cancer eventually go on to die from their disease (Harries, M. & Gore, M. *Part I: chemotherapy for epithelial ovarian cancer-treatment at first diagnosis.* Lancet Oncol. 3, 529-536 (2002)). Major trials published over the past 15 years report that the median PFS for patients with advanced disease ranges between 16 and 23 months while the median OS lies between 31 and 65 months (International Collaborative Ovarian Neoplasm Group. *Paclitaxel plus carboplatin versus standard chemotherapy with either single-agent carboplatin or cyclophosphamide, doxorubicin, and cisplatin in women with ovarian cancer: the ICON3 randomised trial.* Lancet 360, 505-515 (2002); Armstrong, D. K. et al. *Intraperitoneal cisplatin and paclitaxel in ovarian cancer.* N. Engl. J. Med. 354, 34-43 (2006); McGuire, W. P. et al. *Cyclophosphamide and cisplatin compared with paclitaxel and cisplatin in patients with stage III and stage IV ovarian cancer.* N. Engl. J. Med. 334, 1-6 (1996); Muggia, F. M. et al. *Phase III randomized study of cisplatin versus paclitaxel versus cisplatin and paclitaxel in patients with suboptimal stage III or IV ovarian cancer: a gynecologic oncology group study.* J. Clin. Oncol. 18, 106-115 (2000); Piccart, M. J. et al. *Randomized intergroup trial of cisplatin-paclitaxel versus cisplatin-cyclophosphamide in women with advanced epithelial ovarian cancer: three-year results.* J. Natl. Cancer Inst. 92, 699-708 (2000)).

The majority of patients who achieve a CR with first-line chemotherapy ultimately develop recurrent disease. These patients can be subdivided into platinum-sensitive or platinum-resistant groups. 12 In platinum-sensitive patients, disease recurrence occurs more than 6 months after cessation of initial platinum-containing chemotherapy. 12 Platinum-based therapies are typically used to retreat these patients, in light of clinically meaningful responses observed in these patients following a second platinum-based treatment. 13 Currently, there is no optimal treatment strategy for platinum-resistant patients whose disease recurs within 6 months of completing initial platinum-based chemotherapy. 12, 14 Despite a wide range of available treatments, prolonged survival has not been shown in this setting, and ORR is generally less than 20%. 12, 15 As resistant-disease is not curable, the goals of treatment for these patients include palliation of symptoms, prolonged survival and improvements in quality of life. 13, 15, 16

Platinum-resistance is therefore a significant clinical problem for which improved treatment regimens are needed. In particular, bevacizumab (Avastin®), a monoclonal antibody targeted against the pro-angiogenic vascular endothelial growth factor (VEGF), holds significant therapeutic potential.

SUMMARY OF THE INVENTION

The present invention contemplates a method of treating a patient diagnosed with a platinum-resistant ovarian cancer comprising administering to said patient an effective amount of an anti-VEGF antibody and a chemotherapeutic, wherein said patient received two or fewer prior anti-cancer regimens, wherein said treatment prolongs said patient's median progression-free survival time as compared to a platinum-resistant ovarian cancer patient receiving said chemotherapeutic alone. In one embodiment, the platinum-resistant ovarian cancer is an epithelial ovarian cancer (EOC), a fallopian tube carcinoma (FTC), or a primary peritoneal carcinoma (PPC). In another embodiment, the patient is not refractory to previous platinum treatment and/or has measurable disease according to RECIST 1.0 or CA-125 assessable disease according to the GCIG criteria. In a further embodiment, the patient has an ECOG performance status of 0-2 and a life expectancy of at least 12 weeks.

The present invention contemplates a method of treating a patient diagnosed with a platinum-resistant ovarian cancer comprising administering to said patient an effective amount of an anti-VEGF antibody and a chemotherapeutic as described above, where the chemotherapeutic is selected from the group consisting of paclitaxel, topotecan or a pegylated liposomal doxorubicin (PLD). In a further embodiment, the effective amount of said paclitaxel is administered at 80 mg/m$^2$ as a 1 hour intravenous infusion on days 1, 8, 15 and 22 q4w.

In another embodiment in the method described above, the effective amount of said topotecan is administered at 4 mg/m$^2$ as a 30 minute intravenous infusion on days 1, 8 and 15 q4w. In an alternative embodiment in the method described above, the effective amount of said topotecan is administered at 1.25 mg/m$^2$ as a 30 minute intravenous infusion on days 1 to 5 every three weeks.

In another embodiment in the method described above, the effective amount of said PLD is administered at 40 mg/m$^2$ as a 1 mg/min intravenous infusion on day 1 only, then as a 1 hour infusion thereafter, q4w.

In the present invention described above which contemplates a method of treating a patient diagnosed with a platinum-resistant ovarian cancer comprising administering to said patient an effective amount of an anti-VEGF antibody and a chemotherapeutic, the anti-VEGF antibody binds the A4.6.1 epitope. In a further embodiment, the anti-VEGF antibody is bevacizumab. In still a further embodiment, the anti-VEGF antibody comprises a variable heavy chain (VH) and a variable light chain (VL), wherein said VH has an amino acid sequence of SEQ ID NO:2 and said VL has an amino acid sequence of SEQ ID NO:1.

In the present invention described above which contemplates a method of treating a patient diagnosed with a platinum-resistant ovarian cancer comprising administering to said patient an effective amount of an anti-VEGF antibody and a chemotherapeutic, the effective amount of said anti-VEGF antibody is 10 mg/kg intravenously every two weeks and the effective amount of said anti-VEGF antibody is administered initially intravenously over 90 minutes, with subsequent infusions over 60 minutes and then 30 minutes. In a further embodiment, the effective amount of said anti-VEGF antibody is 15 mg/kg intravenously every three weeks, where the anti-VEGF antibody is administered initially intravenously over 90 minutes, with subsequent infusions over 60 minutes and then 30 minutes.

In the present invention described above, the anti-VEGF antibody is administered first to said patient at the first cycle and then subsequent administrations of said anti-VEGF antibody are either prior to or after said chemotherapeutic. In another embodiment, the anti-VEGF antibody is administered concurrently with said chemotherapeutic.

In the present invention described above which contemplates a method of treating a patient diagnosed with a platinum-resistant ovarian cancer comprising administering to said patient an effective amount of an anti-VEGF antibody and a chemotherapeutic, as described above, the median progression-free survival time is prolonged by about 3 months with a hazard ratio (HR) equal to 0.48, as compared to a platinum-resistant ovarian cancer patient receiving said chemotherapeutic alone. In another embodiment, the median progression-free survival time is prolonged by at least 3 months or greater with a hazard ratio (HR) equal to 0.48, as compared to a platinum-resistant ovarian cancer patient receiving said chemotherapeutic alone. In another embodiment, the median progression-free survival time is prolonged by at least 3 months or greater with a hazard ratio (HR) from about 0.32 to about 0.57, as compared to a platinum-resistant ovarian cancer patient receiving said chemotherapeutic alone. In another embodiment, the median progression-free survival time is prolonged by about 3 months with a hazard ratio (HR) from about 0.32 to about 0.57, as compared to a platinum-resistant ovarian cancer patient receiving said chemotherapeutic alone. In yet another embodiment, in the method described above, said chemotherapeutic is paclitaxel and said patient's median progression-free survival time is prolonged by at least 6 months or greater with a hazard ration (HR) of about 0.46 as compared to a platinum-resistant ovarian cancer patient receiving said chemotherapeutic alone. In yet another embodiment, in the method described above, said chemotherapeutic is pegylated liposomal doxorubicin (PLD) and said patient's median progression-free survival time is prolonged by at least 2 months or greater with a hazard ration of about 0.57 as compared to a platinum-resistant ovarian cancer patient receiving said chemotherapeutic alone. In yet another embodiment, in the method described above, said chemotherapeutic is topotecan and said patient's median progression-free survival time is prolonged by at least 3 months or greater with a hazard ratio (HR) of about 0.32 as compared to a platinum-resistant ovarian cancer patient receiving said chemotherapeutic alone. In yet another embodiment in the methods described above, the patient is less than 65 years old. In yet another embodiment in the methods described above, the patient is equal to or greater than 65 years old. In one embodiment in the methods described above, the patient has a platinum free interval (PFI) of less than 3 months. In an alternative embodiment in the methods described above, the patient has a PFI of 3 to 6 months. In one embodiment in the methods described above, the patient has abdominal ascites. In an alternative embodiment in the methods described above, the patient does not have abdominal ascites.

In yet another embodiment, in the method described above, the treatment further improves said patient's objective response rate (ORR) as compared to a platinum-resistant ovarian cancer patient receiving said chemotherapeutic alone. In one embodiment, the ORR is improved by at least 1.5 fold or by at least 2 fold as compared to a platinum-resistant ovarian cancer patient receiving said chemotherapeutic alone. In yet another embodiment, the ORR is improved to about 30.9% as compared to a platinum-resistant ovarian cancer patient receiving said chemotherapeutic alone. In another embodiment, in the method described above, wherein the ORR is improved by at least 1.5 fold as compared to a platinum-resistant ovarian cancer patient receiving said chemotherapeutic alone, the chemotherapeutic is paclitaxel or pegylated liposomal doxorubicin (PLD). In another embodiment, in the method described above, wherein the ORR is improved by at least 2 fold as compared to a platinum-resistant ovarian cancer patient receiving said chemotherapeutic alone, the chemotherapeutic is topotecan.

The present invention also contemplates a kit comprising an anti-VEGF antibody binding essentially to epitope A4.6.1, a chemotherapeutic and a package insert or label with instructions to treat a patient diagnosed with a platinum-resistant ovarian cancer comprising administering to said patient an effective amount of an anti-VEGF antibody and a chemotherapeutic, wherein said patient received two or fewer prior anti-cancer regimens, wherein said treatment prolongs said patient's median progression-free survival time as compared to a platinum-resistant ovarian cancer patient receiving said chemotherapeutic alone. In one embodiment of the kit described above, the platinum-resistant ovarian cancer is an epithelial ovarian cancer (EOC), a fallopian tube carcinoma (FTC), or a primary peritoneal carcinoma (PPC). In another embodiment of the kit described above, the anti-VEGF antibody is bevacizumab and said chemotherapeutic is selected from the group consisting of paclitaxel, topotecan or a pegylated liposomal doxorubicin (PLD).

The present invention further contemplates a method of promoting administration of an anti-VEGF antibody binding essentially to epitope A4.6.1, and a chemotherapeutic to treat platinum-resistant ovarian cancer in a patient, wherein said promotion is by written material. In one embodiment to the promotional method described, the anti-VEGF antibody is bevacizumab, and said chemotherapeutic is selected from the group consisting of paclitaxel, topotecan or a pegylated liposomal doxorubicin (PLD). In another embodiment to the promotional method described, the written material is a package insert or label that accompanies a commercial formulation of said anti-VEGF antibody and said chemotherapeutic.

DETAILED DESCRIPTION OF EMBODIMENTS OF THE INVENTION

Definitions

Figure 1:
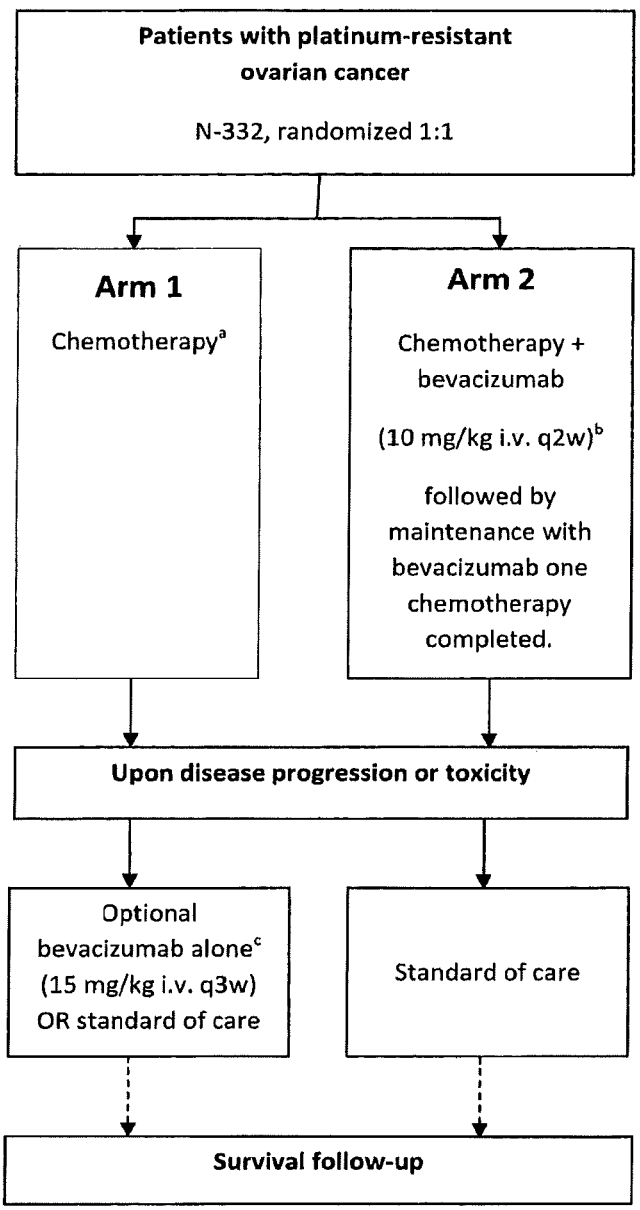
FIG. 1 shows the two-arm Phase III study design treatment sequence as disclosed in more detail in Example 1. In both Arms 1 and 2, there is a choice of chemotherapeutic, eitherpaclitaxel, topotecan or PLD. In Arm 2, for bevacizumab, the alternative dose is 15 mg/kg every three weeks if the chemotherapeutic topotecan is selected and administered at a dose of 1.25 mg/m$^2$ on a 1-5/every three weeks schedule.

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined throughout the specification or known in the art, e.g., but are not limited to, antibodies to VEGF-A or to the VEGF-A receptor (e.g., KDR receptor or Flt-1 receptor), VEGF-trap, anti-PDGFR inhibitors such as Gleevec™ (Imatinib Mesylate). Anti-angiogensis agents also include native angiogenesis inhibitors, e.g., angiostatin, endostatin, etc. See, e.g., Klagsbrun and D'Amore, Annu. Rev. Physiol., 53:217-39 (1991); Streit and Detmar, Oncogene, 22:3172-3179 (2003) (e.g., Table 3 listing anti-angiogenic therapy in malignant melanoma); Ferrara & Alitalo, Nature Medicine 5:1359-1364 (1999); Tonini et al., Oncogene, 22:6549-6556 (2003) (e.g., Table 2 listing known antiangiogenic factors); and Sato. Int. J. Clin. Oncol., 8:200-206 (2003) (e.g., Table 1 lists anti-angiogenic agents used in clinical trials).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "ascites" or abdominal ascites refers to fluid that has accumulated in the abdomen in excess amount. In the presence of ovarian cancer, ascitic fluid often contains free-floating cancer cells which have broken off from the cancerous growths. The presentation of abdominal ascites typically indicates a more symptomatic disease and a poorer outcome as compared to those patients who do not have abdominal ascites.

The term "bevacizumab" refers to a recombinant humanized anti-VEGF monoclonal antibody generated according to Presta et al. (1997) Cancer Res. 57:4593-4599, also known as "rhuMAb VEGF" or "AVASTIN®". It comprises mutated human IgG1 framework regions and antigen-binding complementarity-determining regions from the murine anti-human VEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1. bevacizumab binds to the same epitope as the monoclonal anti-VEGF antibody A4.6.1 produced by hybridoma ATCC HB 10709.

"CA-125" means cancer antigen 125 or carbohydrate antigen 125 is a clinically approved blood test for following the response to treatment and predicting prognosis after treatment. It is especially useful for detecting the recurrence of ovarian cancer. While it is best known as a marker for ovarian cancer, it may also be elevated in other cancers, including endometrial cancer, fallopian tube cancer, lung cancer, breast cancer and gastrointestinal cancer.

The terms "cancer" and "cancerous" refer to or describe the physiological condition in mammals that is typically characterized by unregulated cell growth. Included in this definition are benign and malignant cancers as well as dormant tumors or micrometastatses. Examples of cancer include but are not limited to, carcinoma, lymphoma, blastoma, sarcoma, and leukemia. More particular examples of such cancers include, but is not limited to, ovarian cancers, including epithelial ovarian cancer (EOC), fallopian tube carcinoma (FTC), or primary peritoneal carcinoma (PPC) or platinum-resistant ovarian cancers. Other cancers include, for example, breast cancer, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, liver cancer, bladder cancer, hepatoma, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NEIL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

A "chemotherapeutic agent" is a chemical compound useful in the treatment of cancer. Examples of chemotherapeutic agents include is a chemical compound useful in the treatment of cancer. Examples of chemotherapeutic agents include, for example, paclitaxel or topotecan or pegylated liposomal doxorubicin (PLD). Other examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin; bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® docetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

The term "effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, duration of progression free survival (PFS), the response rates (RR), duration of response, and/or quality of life.

The "epitope A4.6.1" refers to the epitope recognized by the anti-VEGF antibody bevacizumab (AVASTIN®) (see Muller Y et al., Structure 15 Sep. 1998, 6:1153-1167). In certain embodiments of the invention, the anti-VEGF antibodies include, but are not limited to, a monoclonal antibody that binds to the same epitope as the monoclonal anti-VEGF antibody A4.6.1 produced by hybridoma ATCC HB 10709;

a recombinant humanized anti-VEGF monoclonal antibody generated according to Presta et al. (1997) Cancer Res. 57:4593-4599.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).) Unless otherwise indicated, HVR residues and other residues in the variable domain (e.g., FR residues) are numbered herein according to Kabat et al., supra.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

For the methods of the present invention, the term "instructing" a subject means providing directions for applicable therapy, medication, treatment, treatment regimens, and the like, by any means, but preferably in writing, such as in the form of package inserts or other written promotional material.

The term "intravenous infusion" refers to introduction of a drug into the vein of an animal or human subject over a period of time greater than approximately 5 minutes, preferably between approximately 30 to 90 minutes, although, according to the invention, intravenous infusion is alternatively administered for 10 hours or less.

The term "intravenous bolus" or "intravenous push" refers to drug administration into a vein of an animal or human such that the body receives the drug in approximately 15 minutes or less, preferably 5 minutes or less.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

A "maintenance" dose herein refers to one or more doses of a therapeutic agent administered to the subject over or after a treatment period. Usually, the maintenance doses are administered at spaced treatment intervals, such as approximately every week, approximately every 2 weeks, approximately every 3 weeks, or approximately every 4 weeks.

By "maintenance therapy" is meant a therapeutic regimen that is given to reduce the likelihood of disease recurrence or progression Maintenance therapy can be provided for any length of time, including extended time periods up to the life-span of the subject. Maintenance therapy can be provided after initial therapy or in conjunction with initial or additional therapies. Dosages used for maintenance therapy can vary and can include diminished dosages as compared to dosages used for other types of therapy. See also "maintenance" herein.

The term "marketing" is used herein to describe the promotion, selling or distribution of a product (e.g., drug). Marketing specifically includes packaging, advertising, and any business activity with the purpose of commercializing a product.

By "metastasis" or "metastatic" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

By "monotherapy" is meant a therapeutic regimen that includes only a single therapeutic agent for the treatment of the cancer or tumor during the course of the treatment period. Monotherapy using a VEGF-specific antagonist means that the VEGF-specific antagonist is administered in the absence of an additional anti-cancer therapy during treatment period.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject, A pharmaceutically acceptable carrier includes, but is not limited to, a buffer, excipient, stabilizer, or preservative.

"Platinum-resistant" means an ovarian cancer disease progression within less than six (6) months from completion of a minimum of four (4) platinum therapy cycles. The date is calculated from the last administered dose of platinum therapy.

The term "platinum-free interval" (PFI) means the time elapsed since completing platinum-based therapy. In general, the longer the platinum-free interval, the higher the response to retreatment.

For the methods of the present invention, the term "promoting" means offering, advertising, selling, or describing a particular drug, combination of drugs, or treatment modality, by any means, including writing, such as in the form of package inserts. Promoting herein refers to promotion of a therapeutic agent, such as a VEGF antagonist, e.g., anti-VEGF antibody or chemotherapeutic agent, for an indication, such as breast cancer treatment, where such promoting is authorized by the Food and Drug Administration (FDA) as having been demonstrated to be associated with statistically significant therapeutic efficacy and acceptable safety in a population of subjects.

"Progression free survival (PFS)" refers to the time from treatment (or randomization) to first disease progression or death. For example it is the time that the subject remains alive, without return of the cancer, e.g., for a defined period of time such as about 1 month, about 2 months, about 3 months, about 4, months, about 5 months, about 6 months, about 7 months, about 8 months, about 9 months, about 1 year, about 2 years, about 3 years, etc., from initiation of treatment or from initial diagnosis. In one aspect of the invention, PFS can be assessed by Response Evaluation Criteria in Solid Tumors (RECIST).

A "population" of subjects refers to a group of subjects with cancer, such as in a clinical trial, or as seen by oncologists following FDA approval for a particular indication, such as breast cancer therapy.

By "subject" is meant a mammal, including, but not limited to, a human or non-human mammal, such as a bovine, equine, canine, ovine, or feline. Preferably, the subject is a human. Patients are also subjects herein.

"Survival" refers to the subject remaining alive, and includes progression free survival (PFS) and overall survival (OS). Survival can be estimated by the Kaplan-Meier method, and any differences in survival are computed using the stratified log-rank test.

"Overall survival" refers to the subject remaining alive for a defined period of time, such as about 1 year, about 2 years, about 3 years, about 4 years, about 5 years, about 10 years, etc., from initiation of treatment or from initial diagnosis. In the studies underlying the present invention the event used for survival analysis was death from any cause.

"Overall response rate" or "Objective response rate" (ORR)—the percentage of people who experience a decrease in the size (or amount for blood cancers) of the cancer for a minimum amount of time; ORR is the sum of the complete and partial response rates.

By "extending survival" or "increasing the likelihood of survival" is meant increasing PFS and/or OS in a treated subject relative to an untreated subject (i.e. relative to a subject not treated with a VEGF antibody), or relative to a control treatment protocol, such as treatment only with the chemotherapeutic agent, such as those use in the standard of care for ovarian cancers, such as, for example, paclitaxel, topotecan or PLD. Survival is monitored for at least about one month, about two months, about four months, about six months, about nine months, or at least about 1 year, or at least about 2 years, or at least about 3 years, or at least about 4 years, or at least about 5 years, or at least about 10 years, etc., following the initiation of treatment or following the initial diagnosis.

Hazard ratio (HR) is a statistical definition for rates of events. For the purpose of the invention, hazard ratio is defined as representing the probability of an event in the experimental arm divided by the probability of an event in the control arm at any specific point in time. "Hazard ratio" in progression free survival analysis is a summary of the difference between two progression free survival curves, representing the reduction in the risk of death on treatment compared to control, over a period of follow-up.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "VEGF" or "VEGF-A" is used to refer to the 165-amino acid human vascular endothelial cell growth factor and related 121-, 145-, 189-, and 206-amino acid human vascular endothelial cell growth factors, as described by, e.g., Leung et al. Science, 246:1306 (1989), and Houck et al. Mol. Endocrin., 5:1806 (1991), together with the naturally occurring allelic and processed forms thereof. VEGF-A is part of a gene family including VEGF-B, VEGF-C, VEGF-D, VEGF-E, VEGF-F, and PlGF. VEGF-A primarily binds to two high affinity receptor tyrosine kinases, VEGFR-1 (Flt-1) and VEGFR-2 (Flk-1/KDR), the latter being the major transmitter of vascular endothelial cell mitogenic signals of VEGF-A. Additionally, neuropilin-1 has been identified as a receptor for heparin-binding VEGF-A isoforms, and may play a role in vascular development. The term "VEGF" or "VEGF-A" also refers to VEGFs from non-human species such as mouse, rat, or primate. Sometimes the VEGF from a specific species is indicated by terms such as hVEGF for human VEGF or mVEGF for murine VEGF. Typically, VEGF refers to human VEGF. The term "VEGF" is also used to refer to truncated forms or fragments of the polypeptide comprising amino acids 8 to 109 or 1 to 109 of the 165-amino acid human vascular endothelial cell growth factor. Reference to any such forms of VEGF may be identified in the application, e.g., by "VEGF (8-109)," "VEGF (1-109)" or "VEGF165." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

An "anti-VEGF antibody" is an antibody that binds to VEGF with sufficient affinity and specificity. The antibody selected will normally have a binding affinity for VEGF, for example, the antibody may bind hVEGF with a Kd value of between 100 nM-1 pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example. In certain embodiments, the anti-VEGF antibody of the invention can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as PlGF, PDGF or bFGF.

A "VEGF antagonist" refers to a molecule capable of neutralizing, blocking, inhibiting, abrogating, reducing or interfering with VEGF activities including its binding to one or more VEGF receptors. VEGF antagonists include anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases.

A "chimeric VEGF receptor protein" is a VEGF receptor molecule having amino acid sequences derived from at least two different proteins, at least one of which is a VEGF receptor protein. In certain embodiments, the chimeric VEGF receptor protein is capable of binding to and inhibiting the biological activity of VEGF.

Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Anti-VEGF Antibodies and Antagonists

The VEGF antigen to be used for production of VEGF antibodies may be, e.g., the $VEGF_{165}$ molecule as well as other isoforms of VEGF or a fragment thereof containing the desired epitope. In one embodiment, the desired epitope is the one recognized by bevacizumab, which binds to the same epitope as the monoclonal anti-VEGF antibody A4.6.1 produced by hybridoma ATCC HB 10709 (known as "epitope A.4.6.1" defined herein). Other forms of VEGF useful for generating anti-VEGF antibodies of the invention will be apparent to those skilled in the art.

Human VEGF was obtained by first screening a cDNA library prepared from human cells, using bovine VEGF cDNA as a hybridization probe. Leung et al. (1989) Science, 246:1306. One cDNA identified thereby encodes a 165-amino acid protein having greater than 95% homology to bovine VEGF; this 165-amino acid protein is typically referred to as human VEGF (hVEGF) or $VEGF_{165}$. The mitogenic activity of human VEGF was confirmed by expressing the human VEGF cDNA in mammalian host cells. Media conditioned by cells transfected with the human VEGF cDNA promoted the proliferation of capillary endothelial cells, whereas control cells did not. Leung et al. (1989) Science, supra. Further efforts were undertaken to clone and express VEGF via recombinant DNA techniques. (See, e.g., Ferrara, Laboratory Investigation 72:615-618 (1995), and the references cited therein).

VEGF is expressed in a variety of tissues as multiple homodimeric forms (121, 145, 165, 189, and 206 amino acids per monomer) resulting from alternative RNA splicing. VEGF$_{121}$ is a soluble mitogen that does not bind heparin; the longer forms of VEGF bind heparin with progressively higher affinity. The heparin-binding forms of VEGF can be cleaved in the carboxy terminus by plasmin to release a diffusible form(s) of VEGF. Amino acid sequencing of the carboxy terminal peptide identified after plasmin cleavage is Arg$_{110}$-Ala$_{111}$. Amino terminal "core" protein, VEGF (1-110) isolated as a homodimer, binds neutralizing monoclonal antibodies (such as the antibodies referred to as 4.6.1 and 3.2E3.1.1) and soluble forms of VEGF receptors with similar affinity compared to the intact VEGF$_{165}$ homodimer.

Several molecules structurally related to VEGF have also been identified recently, including placenta growth factor (PlGF), VEGF-B, VEGF-C, VEGF-D and VEGF-E. Ferrara and Davis-Smyth (1987) Endocr. Rev., supra; Ogawa et al. J. Biological Chem. 273:31273-31281 (1998); Meyer et al. EMBO J., 18:363-374 (1999). A receptor tyrosine kinase, Flt-4 (VEGFR-3), has been identified as the receptor for VEGF-C and VEGF-D. Joukov et al. EMBO. J. 15:1751 (1996); Lee et al. Proc. Natl. Acad. Sci. USA 93:1988-1992 (1996); Achen et al. (1998) Proc. Natl. Acad. Sci. USA 95:548-553. VEGF-C has been shown to be involved in the regulation of lymphatic angiogenesis. Jeltsch et al. Science 276:1423-1425 (1997).

Two VEGF receptors have been identified, Flt-1 (also called VEGFR-1) and KDR (also called VEGFR-2). Shibuya et al. (1990) Oncogene 8:519-527; de Vries et al. (1992) Science 255:989-991; Terman et al. (1992) Biochem. Biophys. Res. Commun. 187:1579-1586. Neuropilin-1 has been shown to be a selective VEGF receptor, able to bind the heparin-binding VEGF isoforms (Soker et al. (1998) Cell 92:735-45).

Anti-VEGF antibodies that are useful in the methods of the invention include any antibody, or antigen binding fragment thereof, that bind with sufficient affinity and specificity to VEGF and can reduce or inhibit the biological activity of VEGF. An anti-VEGF antibody will usually not bind to other VEGF homologues such as VEGF-B or VEGF-C, nor other growth factors such as PlGF, PDGF, or bFGF.

In certain embodiments of the invention, the anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) Cancer Res. 57:4593-4599. In one embodiment, the anti-VEGF antibody is "bevacizumab (BV)", also known as "rhuMAb VEGF" or "AVASTIN®". It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1.

Bevacizumab (AVASTIN®) was the first anti-angiogenesis therapy approved by the FDA and is approved for the treatment metastatic colorectal cancer (first- and second-line treatment in combination with intravenous 5-FU-based chemotherapy), advanced non-squamous, non-small cell lung cancer (NSCLC) (first-line treatment of unresectable, locally advanced, recurrent or metastatic NSCLC in combination with carboplatin and paclitaxel) and metastatic HER2-negative breast cancer (previously untreated, metastatic HER2-negative breast cancer in combination with paclitaxel).

Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, and U.S. Patent Application 60/991,302, the content of these patent applications are expressly incorporated herein by reference. For additional antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., Journal of Immunological Methods 288:149-164 (2004). Other antibodies include those that bind to a functional epitope on human VEGF comprising of residues F17, M18, D19, Y21, Y25, Q89, I91, K101, E103, and C104 or, alternatively, comprising residues F17, Y21, Q22, Y25, D63, 183 and Q89.

In one embodiment of the invention, the anti-VEGF antibody has a light chain variable region comprising the following amino acid sequence:

```
                                        (SEQ ID NO: 1)
DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR.
``` and a heavy chain variable region comprising the following amino acid sequence:

```
                                        (SEQ ID NO: 2)
EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT

VSS
```

A "G6 series antibody" according to this invention, is an anti-VEGF antibody that is derived from a sequence of a G6 antibody or G6-derived antibody according to any one of FIGS. 7, 24-26, and 34-35 of PCT Publication No. WO2005/012359, the entire disclosure of which is expressly incorporated herein by reference. See also PCT Publication No. WO2005/044853, the entire disclosure of which is expressly incorporated herein by reference. In one embodiment, the G6 series antibody binds to a functional epitope on human VEGF comprising residues F17, Y21, Q22, Y25, D63, 183 and Q89.

A "B20 series antibody" according to this invention is an anti-VEGF antibody that is derived from a sequence of the B20 antibody or a B20-derived antibody according to any one of FIGS. 27-29 of PCT Publication No. WO2005/012359, the entire disclosure of which is expressly incorporated herein by reference. See also PCT Publication No. WO2005/044853, and U.S. Patent Application 60/991,302, the content of these patent applications are expressly incorporated herein by reference. In one embodiment, the B20 series antibody binds to a functional epitope on human VEGF comprising residues F17, M18, D19, Y21, Y25, Q89, I91, K101, E103, and C104.

A "functional epitope" according to this invention refers to amino acid residues of an antigen that contribute energetically to the binding of an antibody. Mutation of any one of the energetically contributing residues of the antigen (for example, mutation of wild-type VEGF by alanine or homolog mutation) will disrupt the binding of the antibody such that the relative affinity ratio (IC50 mutant VEGF/IC50 wild-type VEGF) of the antibody will be greater than 5 (see Example 2 of WO2005/012359). In one embodiment, the relative affinity ratio is determined by a solution binding phage displaying ELISA. Briefly, 96-well Maxisorp immunoplates (NUNC) are coated overnight at 4.degree. C. with an Fab form of the antibody to be tested at a concentration of 2 ug/ml in PBS, and blocked with PBS, 0.5% BSA, and 0.05% Tween20 (PBT) for 2 h at room temperature. Serial dilutions of phage displaying hVEGF alanine point mutants (residues 8-109 form) or wild type hVEGF (8-109) in PBT are first incubated on the Fab-coated plates for 15 min at room temperature, and the plates are washed with PBS, 0.05% Tween20 (PBST). The bound phage is detected with an anti-M13 monoclonal antibody horseradish peroxidase (Amersham Pharmacia) conjugate diluted 1:5000 in PBT, developed with 3,3',5,5'-tetramethylbenzidine (TMB, Kirkegaard & Perry Labs, Gaithersburg, Md.) substrate for approximately 5 min, quenched with 1.0 M H3PO4, and read spectrophotometrically at 450 nm. The ratio of IC50 values (IC50, ala/IC50, wt) represents the fold of reduction in binding affinity (the relative binding affinity).

VEGF Receptor Molecules

The two best characterized VEGF receptors are VEGFR1 (also known as Flt-1) and VEGFR2 (also known as KDR and FLK-1 for the murine homolog). The specificity of each receptor for each VEGF family member varies but VEGF-A binds to both Flt-1 and KDR. Both Flt-I and KDR belong to the family of receptor tyrosine kinases (RTKs). The RTKs comprise a large family of transmembrane receptors with diverse biological activities. At least nineteen (19) distinct RTK subfamilies have been identified. The receptor tyrosine kinase (RTK) family includes receptors that are crucial for the growth and differentiation of a variety of cell types (Yarden and Ullrich (1988) Ann. Rev. Biochem. 57:433-478; Ullrich and Schlessinger (1990) Cell 61:243-254). The intrinsic function of RTKs is activated upon ligand binding, which results in phosphorylation of the receptor and multiple cellular substrates, and subsequently in a variety of cellular responses (Ullrich & Schlessinger (1990) Cell 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see, Schlessinger and Ullrich (1992) Neuron 9:1-20. Structurally, both Flt-1 and KDR have seven immunoglobulin-like domains in the extracellular domain, a single transmembrane region, and a consensus tyrosine kinase sequence which is interrupted by a kinase-insert domain. Matthews et al. (1991) Proc. Natl. Acad. Sci. USA 88:9026-9030; Terman et al. (1991) Oncogene 6:1677-1683. The extracellular domain is involved in the binding of VEGF and the intracellular domain is involved in signal transduction.

VEGF receptor molecules, or fragments thereof, that specifically bind to VEGF can be used in the methods of the invention to bind to and sequester the VEGF protein, thereby preventing it from signaling. In certain embodiments, the VEGF receptor molecule, or VEGF binding fragment thereof, is a soluble form, such as sFlt-1. A soluble form of the receptor exerts an inhibitory effect on the biological activity of the VEGF protein by binding to VEGF, thereby preventing it from binding to its natural receptors present on the surface of target cells. Also included are VEGF receptor fusion proteins, examples of which are described below.

A chimeric VEGF receptor protein is a receptor molecule having amino acid sequences derived from at least two different proteins, at least one of which is a VEGF receptor protein (e.g., the flt-1 or KDR receptor), that is capable of binding to and inhibiting the biological activity of VEGF. In certain embodiments, the chimeric VEGF receptor proteins of the invention consist of amino acid sequences derived from only two different VEGF receptor molecules; however, amino acid sequences comprising one, two, three, four, five, six, or all seven Ig-like domains from the extracellular ligand-binding region of the flt-1 and/or KDR receptor can be linked to amino acid sequences from other unrelated proteins, for example, immunoglobulin sequences. Other amino acid sequences to which Ig-like domains are combined will be readily apparent to those of ordinary skill in the art. Examples of chimeric VEGF receptor proteins include, e.g., soluble Flt-1/Fc, KDR/Fc, or FLt-1/KDR/Fc (also known as VEGF Trap). (See for example PCT Application Publication No. WO97/44453).

A soluble VEGF receptor protein or chimeric VEGF receptor proteins of the invention includes VEGF receptor proteins which are not fixed to the surface of cells via a transmembrane domain. As such, soluble forms of the VEGF receptor, including chimeric receptor proteins, while capable of binding to and inactivating VEGF, do not comprise a transmembrane domain and thus generally do not become associated with the cell membrane of cells in which the molecule is expressed.

Therapeutic Uses and Compositions

The invention encompasses anti-angiogenic therapy, a novel cancer treatment strategy aimed at inhibiting the development of tumor blood vessels required for providing nutrients to support tumor growth. Because angiogenesis is involved in both primary tumor growth and metastasis, the anti-angiogenic treatment provided by the invention is capable of inhibiting the neoplastic growth of tumor at the primary site as well as preventing metastasis of tumors at the secondary sites, therefore allowing attack of the tumors by other therapeutics.

Specifically, provided herein are methods of treating a subject diagnosed with platinum-resistant ovarian cancer, comprising administering to the subject a treatment regimen combining an effective amount of a chemotherapeutic and an anti-VEGF antibody. Additionally, the subject is not refractory to prior treatment of ovarian cancer and had only had two or fewer prior anti-cancer regimens. The treatment regimen combining the chemotherapy and the administration of the anti-VEGF antibody extends the progression free survival (PFS) of the subject.

Combination Therapies

The invention features the use or compositions of a combination of an anti-VEGF antibody with one or more additional anti-cancer therapies. Examples of anti-cancer therapies include, without limitation, surgery, radiation therapy (radiotherapy), biotherapy, immunotherapy, chemotherapy, or a combination of these therapies. In addition, cytotoxic agents, anti-angiogenic and anti-proliferative agents can be used in combination with the anti-VEGF antibody.

In certain aspects of any of the methods and uses, the invention provides treating breast cancer, by administering effective amounts of an anti-VEGF antibody and a chemotherapeutic agent to a subject diagnosed with platinum-resistant ovarian cancer. A variety of chemotherapeutic agents may be used in the combined treatment methods and uses of the invention. An exemplary and non-limiting list of chemotherapeutic agents contemplated is provided herein under "Definition", or described herein. In one embodiment, the chemotherapeutic agent is paclitaxel. In another embodiment, the chemotherapeutic agent is topotecan. In yet another embodiment, the chemotherapeutic agent is pegylated liposomal doxorubicin (PLD).

In one example, the combined treatment contemplated above involves administration which includes simultaneous administration, using separate formulations or a single pharmaceutical formulation, and consecutive administration in either order, wherein preferably there is a time period while both (or all) active agents simultaneously exert their biological activities. Preparation and dosing schedules for such chemotherapeutic agents may be used according to manufacturers' instructions or as determined empirically by the skilled practitioner. Preparation and dosing schedules for chemotherapy are also described in Chemotherapy Service Ed., M. C. Perry, Williams & Wilkins, Baltimore, Md. (1992). The chemotherapeutic agent may precede, or follow administration of the anti-VEGF antibody or may be given simultaneously therewith.

In some other aspects of any of the methods and uses, other therapeutic agents useful for combination tumor therapy with the antibody of the invention include antagonist of other factors that are involved in tumor growth, such as EGFR, ErbB3, ErbB4, or TNF. Sometimes, it may be beneficial to also administer one or more cytokines to the subject. In one embodiment, the VEGF antibody is co-administered with a growth inhibitory agent. For example, the growth inhibitory agent may be administered first, followed by the VEGF antibody. However, simultaneous administration or administration of the VEGF antibody first is also contemplated. Suitable dosages for the growth inhibitory agent are those presently used and may be lowered due to the combined action (synergy) of the growth inhibitory agent and anti-VEGF antibody.

The formulation herein may also contain more than one active compound as necessary for the particular indication being treated, preferably those with complementary activities that do not adversely affect each other. For example, it may be desirable to further provide antibodies which bind to EGFR, VEGF (e.g. an antibody which binds a different epitope or same epitope on VEGF), VEGFR, or ErbB2 (e.g., Herceptin®) in the one formulation. Alternatively, or in addition, the composition may comprise a chemotherapeutic agent, or a cytotoxic agent. Such molecules are suitably present in combination in amounts that are effective for the purpose intended.

In certain aspects of any of the methods and uses, other therapeutic agents useful for combination cancer therapy with the antibody of the invention include other anti-angiogenic agents. Many anti-angiogenic agents have been identified and are known in the arts, including those listed by Carmeliet and Jain (2000). In one embodiment, the anti-VEGF antibody of the invention is used in combination with another VEGF antagonist or a VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof. Alternatively, or in addition, two or more anti-VEGF antibodies may be co-administered to the subject.

For the prevention or treatment of disease, the appropriate dosage of VEGF-specific antagonist will depend on the type of disease to be treated, as defined above, the severity and course of the disease, whether the VEGF-specific antagonist is administered for preventive or therapeutic purposes, previous therapy, the subject's clinical history and response to the VEGF-specific antagonist, and the discretion of the attending physician. The VEGF-specific antagonist is suitably administered to the subject at one time or over a series of treatments. In a combination therapy regimen, the VEGF-specific antagonist and the one or more anti-cancer therapeutic agent of the invention are administered in a therapeutically effective or synergistic amount. As used herein, a therapeutically effective amount is such that co-administration of a VEGF-specific antagonist and one or more other therapeutic agents, or administration of a composition of the invention, results in reduction or inhibition of the cancer as described above. A therapeutically synergistic amount is that amount of a VEGF-specific antagonist and one or more other therapeutic agents necessary to synergistically or significantly reduce or eliminate conditions or symptoms associated with a particular disease.

The VEGF-specific antagonist and the one or more other therapeutic agents can be administered simultaneously or sequentially in an amount and for a time sufficient to reduce or eliminate the occurrence or recurrence of a tumor, a dormant tumor, or a micrometastases. The VEGF-specific antagonist and the one or more other therapeutic agents can be administered as maintenance therapy to prevent or reduce the likelihood of recurrence of the tumor.

As will be understood by those of ordinary skill in the art, the appropriate doses of chemotherapeutic agents or other anti-cancer agents will be generally around those already employed in clinical therapies, e.g., where the chemotherapeutics are administered alone or in combination with other chemotherapeutics. Variation in dosage will likely occur depending on the condition being treated. The physician administering treatment will be able to determine the appropriate dose for the individual subject.

In addition to the above therapeutic regimes, the subject may be subjected to radiation therapy.

In certain embodiments of any of the methods, uses and compositions, the administered VEGF antibody is an intact, naked antibody. However, the VEGF antibody may be conjugated with a cytotoxic agent. In certain embodiments of any of the methods and uses, the conjugated antibody and/or antigen to which it is bound is/are internalized by the cell, resulting in increased therapeutic efficacy of the conjugate in killing the cancer cell to which it binds. In one embodiment, the cytotoxic agent targets or interferes with nucleic acid in the cancer cell. Examples of such cytotoxic agents include maytansinoids, calicheamicins, ribonucleases and DNA endonucleases.

The invention also features a method of instructing a human subject with platinum-resistant ovarian cancer or a health care provider by providing instructions to receive treatment with an anti-VEGF antibody in combination with a chemotherapeutic and one or more other therapeutic agent so as to increase the time for progression free survival, to decrease the subject's risk of cancer recurrence or to increase the subject's likelihood of survival. In some embodiments the method further comprises providing instructions to receive treatment with at least one chemotherapeutic agent. The treatment with the anti-VEGF antibody may be concurrent with or sequential to the treatment with the chemotherapeutic agent. In certain embodiments the subject is treated as instructed by the method of instructing. Treatment of platinum-resistant ovarian cancer by administration of an anti-VEGF antibody with or without chemotherapy may be continued until cancer recurrence or death.

The invention further provides a promotional method, comprising promoting the administration of an anti-VEGF antibody and one or more other therapeutic agents for treatment of platinum-resistant ovarian cancer in a human subject. In some embodiments the method further comprises promoting the administration of at least one chemotherapeutic agent. Administration of the anti-VEGF antibody may be concurrent with or sequential to administration of the chemotherapeutic agent. Promotion may be conducted by any means available. In some embodiments the promotion is by a package insert accompanying a commercial formulation of the anti-VEGF antibody. The promotion may also be by a package insert accompanying a commercial formulation of the chemotherapeutic agent. Promotion may be by written or oral communication to a physician or health care provider. In some embodiments the promotion is by a package insert where the package inset provides instructions to receive platinum-resistant ovarian cancer therapy with anti-VEGF antibody in combination with one or more other therapeutic agents. In a further embodiment, the package insert include some or all of the results under Example 1. In some embodiments the promotion is followed by the treatment of the subject with the anti-VEGF antibody with the chemotherapeutic agent.

The invention provides a business method, comprising marketing an anti-VEGF antibody in combination with one or more other therapeutic agents for treatment of platinum-resistant ovarian cancer in a human subject so as to increase the subject's time for progression free survival, to decrease the subject's likelihood of cancer recurrence or increase the subject's likelihood of survival. In some embodiments the method further comprises marketing a chemotherapeutic agent for use in combination with the anti-VEGF antibody. In some embodiments the marketing is followed by treatment of the subject with the anti-VEGF antibody with the chemotherapeutic agent.

Also provided is a business method, comprising marketing a chemotherapeutic agent in combination with an anti-VEGF antibody for treatment of ovarian cancer, particularly platinum-resistant ovarian cancers, in a human subject so as to increase the subject's time for progression free survival, to decrease the subject's likelihood of cancer recurrence or increase the subject's likelihood of survival. In some embodiments, the marketing is followed by treatment of the subject with the combination of the chemotherapeutic agent and the anti-VEGF antibody.

Dosages and Duration

The invention will be formulated, dosed, and administered in a fashion consistent with good medical practice. Factors for consideration in this context include the particular disorder being treated, the particular subject being treated, the clinical condition of the individual subject, the cause of the disorder, the site of delivery of the agent, the method of administration, the scheduling of administration, and other factors known to medical practitioners. The "therapeutically effective amount" of the invention to be administered will be governed by such considerations, and is the minimum amount necessary to prevent, ameliorate, or treat, or stabilize, the cancer; to increase the time until progression (duration of progression free survival) or to treat or prevent the occurrence or recurrence of a tumor, a dormant tumor, or a micrometastases. The VEGF-specific antagonist need not be, but is optionally, formulated with one or more agents currently used to prevent or treat cancer or a risk of developing a cancer. The effective amount of such other agents depends on the amount of VEGF-specific antagonist present in the formulation, the type of disorder or treatment, and other factors discussed above. These are generally used in the same dosages and with administration routes as used hereinbefore or about from 1 to 99% of the heretofore employed dosages.

Depending on the type and severity of the disease, about 1 ug/kg to 100 mg/kg (e.g., 0.1-20 mg/kg) of either the anti-VEGF antibody as an initial candidate dosage for administration to the subject, whether, for example, by one or more separate administrations, or by continuous infusion. In one embodiment, desirable dosages include, for example, 6 mg/kg, 8 mg/kg, 10 mg/kg, and 15 mg/kg. For repeated administrations or cycles over several days or longer, depending on the condition, the treatment is sustained until the cancer is treated, as measured by the methods described above or known in the art. However, other dosage regimens may be useful. In one example, the anti-VEGF antibody is administered once every week, every two weeks, or every three weeks, at a dose range from about 6 mg/kg to about 15 mg/kg, including but not limited to 6 mg/kg, 8 mg/kg, 10 mg/kg or 15 mg/kg. The progress of the therapy of the invention is easily monitored by conventional techniques and assays. In other embodiments, such dosing regimen is used in combination with a chemotherapy regimen in platinum-resistant ovarian cancers. Further information about suitable dosages is provided in the Example 1 below.

The duration of therapy will continue for as long as medically indicated or until a desired therapeutic effect (e.g., those described herein) is achieved. In certain embodiments, the claimed therapy is continued for 1 month, 2 months, 4 months, 6 months, 8 months, 10 months, 1 year, 2 years, 3 years, 4 years, 5 years, or for a period of years up to the lifetime of the subject.

The VEGF-specific antagonists of the invention are administered to a subject, e.g., a human subject, in accord with known methods, such as intravenous administration as a bolus or by continuous infusion over a period of time, by intramuscular, intraperitoneal, intracerebrospinal, subcutaneous, intra-articular, intrasynovial, intrathecal, oral, topical, or inhalation routes. Local administration is particularly desired if extensive side effects or toxicity is associated with the VEGF antagonist. An ex vivo strategy can also be used for therapeutic applications. Ex vivo strategies involve transfecting or transducing cells obtained from the subject with a polynucleotide encoding a VEGF antagonist. The transfected or transduced cells are then returned to the subject. The cells can be any of a wide range of types including, without limitation, hematopoietic cells (e.g., bone marrow cells, macrophages, monocytes, dendritic cells, T cells, or B cells), fibroblasts, epithelial cells, endothelial cells, keratinocytes, or muscle cells.

For example, if the VEGF-specific antagonist is an antibody, the antibody is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Preferably the dosing is given by injections, most preferably intravenous or subcutaneous injections, depending in part on whether the administration is brief or chronic.

In another example, the VEGF antibody is administered locally, e.g., by direct injections, when the disorder or location of the tumor permits, and the injections can be repeated periodically. The VEGF antibody can also be delivered systemically to the subject or directly to the tumor cells, e.g., to a tumor or a tumor bed following surgical excision of the tumor, in order to prevent or reduce local recurrence or metastasis, for example of a dormant tumor or micrometastases.

Pharmaceutical Formulations

Therapeutic formulations of the antibodies described herein, used in accordance with the invention, are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized anti-VEGF antibody formulations are described in WO 97/04801, expressly incorporated herein by reference.

Optionally, but preferably, the formulation contains a pharmaceutically acceptable salt, typically, e.g., sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the invention can include a pharmaceutically acceptable surfactant at a concentration of 0.005 to 0.02%.

Typically, bevacizumab is supplied for therapeutic uses in 100 mg and 400 mg preservative-free, single-use vials to deliver 4 ml or 16 ml of bevacizumab (25 mg/ml). The 100 mg product is formulated in 240 mg α, α-trehalose dehydrate, 23.2 mg sodium phosphate (monobasic, monohydrate), 4.8 mg sodium phosphate (dibasic, anhydrous), 1.6 mg polysorbate 20, and Water for Injection, USP. The 400 mg product is formulated in 960 mg α, α-trehalose dehydrate, 92.8 mg sodium phosphate (monobasic, monohydrate), 19.2 mg sodium phosphate (dibasic, anhydrous), 6.4 mg polysorbate 20, and Water for Injection, USP. See also the label for bevacizumab.

The formulation herein may also contain more than one active compound as necessary for the particular indication being treated, preferably those with complementary activities that do not adversely affect each other. For example, it may be desirable to further provide antibodies which bind to VEGF (e.g. an antibody which binds a different epitope on VEGF), VEGFR in the one formulation. Alternatively, or in addition, the composition may comprise a cytotoxic agent, cytokine, growth inhibitory agent and/or VEGFR antagonist. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37.degree. C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations to be used for in vivo administration may be sterile. This is readily accomplished by filtration through sterile filtration membranes.

Efficacy of the Treatment

The main advantage of the of any of the methods, uses and compositions provided herein is the ability of producing marked anti-cancer effects in a human subject without causing significant toxicities or adverse effects, so that the subject benefited from the treatment overall. In one embodiment of any of the methods, uses or compositions, the safety profile is comparable to previous bevacizumab phase III studies. The efficacy of the treatment of the invention can be measured by various endpoints commonly used in evaluating cancer treatments, including but not limited to, tumor regression, tumor weight or size shrinkage, time to progression, duration of survival, progression free survival, overall response rate, duration of response, and quality of life.

Kits

In another embodiment of the invention, an article of manufacture containing materials useful for the treatment of the disorders described above is provided. The article of manufacture comprises a container, a label and a package insert. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an anti-VEGF antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, and syringes. In addition, the article of manufacture comprises a package inserts with instructions for use, including for example instructing the user of the composition to administer the anti-VEGF antibody composition and a chemotherapeutic agent to the subject, e.g., paclitaxel, topotecan or PLD or combinations thereof. The package insert may optionally contain some or all of the results found in Example 1.

The anti-VEGF antibody can be packaged alone or in combination with other anti-cancer therapeutic compounds as a kit. The kit can include optional components that aid in the administration of the unit dose to subjects, such as vials for reconstituting powder forms, syringes for injection, customized IV delivery systems, inhalers, etc. Additionally, the unit dose kit can contain instructions for preparation and administration of the compositions. In certain embodiments, the instruction comprises instructions for use, including for example instructing the user of the composition to administer the anti-VEGF antibody composition and a chemotherapeutic agent to the subject, e.g., paclitaxel, topotecan or PLD or combinations thereof. The instructions may optionally contain some or all of the results found in Example 1. The kit may be manufactured as a single use unit dose for one subject, multiple uses for a particular subject (at a constant dose or in which the individual compounds may vary in potency as therapy progresses); or the kit may contain multiple doses suitable for administration to multiple subjects ("bulk packaging"). The kit components may be assembled in cartons, blister packs, bottles, tubes, and the like.

EXAMPLE

The following are examples of methods and compositions of the invention. It is understood that various other embodiments may be practiced, given the general description provided above.

Example 1—A Multi-Centre, Open-Label, Randomised, Two-Arm Phase III Trial of Bevacizumab Plus Chemotherapy Versus Chemotherapy Alone in Patients with Platinum-Resistant, Epithelial Ovarian, Fallopian Tube or Primary Peritoneal Cancer (AURELIA)

The AURELIA trial evaluated the efficacy and safety of bevacizumab in combination with chemotherapy for platinum-resistant ovarian cancer. This study was designed as a prospective, open-label, randomised, two-arm Phase III evaluation of bevacizumab plus chemotherapy versus chemotherapy alone. To be eligible, patients must have ovarian cancer that progressed within 6 months of previous platinum-based therapy. Paclitaxel, topotecan or pegylated liposomal doxorubicin (PLD) was selected as chemotherapeutic combination partners since they are commonly used for treatment of platinum-resistant disease. By adding bevacizumab to chemotherapy, the AURELIA trial aimed to improve PFS for this group of patients who have limited therapeutic options and face a particularly poor prognosis. The primary objective was to compare progression-free survival (PFS) of patients randomised to selected chemotherapy only or to selected chemotherapy plus bevacizumab.

Study Design—This trial consisted of two (2) treatment arms: chemotherapy-alone (Arm 1) and chemotherapy plus bevacizumab (Arm 2). Patients were randomly assigned (1:1) to either arm, see FIG. 1.

Arm 1 (Chemotherapy Alone):

Eligible patients received one of the following chemotherapies on a 4-week cycle at the discretion of the investigator:

a. Paclitaxel 80 mg/m$^2$ as a 1-hour i.v. infusion on days 1, 8, 15 and 22 q4w.

b. Topotecan 4 mg/m$^2$ as a 30 minute i.v. infusion on days 1, 8 and 15 q4w. Alternatively, a 1.25 mg/m$^2$ dose can be administered over 30 minutes on days 1-5 every three weeks.

c. Pegylated liposomal doxorubicin 40 mg/m$^2$ as a 1 mg/min i.v. infusion on day 1 only, q4w. After cycle 1, the drug can be delivered as a 1 h infusion.

Depending on the chosen chemotherapy, pre-medication was implemented according to local practices. Upon disease progression, patients in Arm 1 had the option of receiving either: (a) bevacizumab alone (15 mg/kg i.v. every three weeks); or (b) standard of care.

Arm 2 (Chemotherapy Plus Bevacizumab):

The chemotherapy was selected from one of those described in Arm 1 at the discretion of the investigator. The chosen chemotherapy was initially combined with bevacizumab 10 mg/kg i.v. every two weeks (or 15 mg/kg every three weeks if used in combination with topotecan 1.25 mg/m$^2$ on days 1-5 of a every three weeks schedule). The initial bevacizumab infusion was over 90 minutes, with subsequent infusions over 60 minutes and then 30 minutes, as tolerated. Bevacizumab was administered before the chemotherapy at the first cycle and then administered prior or after the chemotherapy at subsequent cycles. In case chemotherapy was completed before diagnosis of progressive disease, patients continued to receive bevacizumab as either: (a) 10 mg/kg i.v. every two weeks; or (b) 15 mg/kg every three weeks if topotecan was selected and administered at a dose of 1.25 mg/m$^2$ on days 1-5 of a every three weeks schedule. After disease progression, patients received standard of care treatment.

Analyses of PFS and ORR was based on tumour assessments (based on RECIST criteria) using cross sectional imaging (preferably by CT or MRI in case of contrast allergy) of the pelvis and abdomen and (by X-ray or preferably by CT-scan) of the chest. The same assessment technique was used throughout the study to evaluate a particular lesion.

Tumour assessments were performed at baseline then every 8 weeks (every 9 weeks for patients treated with 1.25 mg/m$^2$ topotecan on days 1-5 of a every three weeks cycle).

Responses were confirmed by a second CT scan performed not earlier than 4 weeks after the criteria for response were first met.

Progressive serial elevation of serum CA-125 were used to determine CA-125 response and biological progression-free interval (PFIbio). Overall survival was measured from the date of randomisation to the date of death from any cause.

Study Population—Inclusion Criteria

Patients ≥18 years of age and a histologically confirmed and documented disease. The following histological types are eligible: adenocarcinoma NOS; clear cell adenocarcinoma; endometriod adenocarcinoma; malignant Brenner's tumour; mixed epithelial carcinoma; mucinous adenocarcinoma; serous adenocarcinoma; transitional cell carcinoma; undifferentiated carcinoma.

Patients must have platinum-resistant disease, (defined as progression within <6 months from completion of a minimum of 4 platinum therapy cycles. The date should be calculated from the last administered dose of platinum therapy).

Patients must have disease that is measurable according to RECIST or assessable according to the Gynecologic Cancer InterGroup (GCIG) CA-125 criteria and require chemotherapy treatment, as well as an ECOG PS 0-2 and a life expectancy of ≥12 weeks.

Study Population—Exclusion criteria

Cancer-related: Patients whose disease was refractory to their previous platinum treatment. Refractory disease is defined as those patients who progressed during the preceding platinum treatment; non-epithelial, including malignant mixed Müllerian tumours; ovarian tumours with low malignant potential (i.e. borderline tumours); history of other clinically active malignancy within 5 years of enrollment, except for tumours with a negligible risk for metastasis or death, such as adequately controlled basal-cell carcinoma or squamous-cell carcinoma of the skin or carcinoma in situ of the cervix or breast.

Prior, Current or Planned Treatment:

Previous treatment with >2 anticancer regimen; any prior radiotherapy to the pelvis or abdomen; surgery (including open biopsy) within 4 weeks prior to the start of study, or anticipation of the need for major surgery during study treatment; minor surgical procedures, within 24 hours prior to the first study treatment; previous exposure to murine CA-125 antibody (only applicable to those patients with non-measurable disease by RECIST); current or recent (within 10 days prior to the first study drug dose) chronic daily treatment with aspirin (>325 mg/day); current or recent treatment with another investigational drug within 30 days of first study treatment dosing or earlier participation in this study; chronic daily treatment with corticosteroids (dose >10 mg/day methylprednisolone equivalent), excluding inhaled steroids.

Laboratory:

Inadequate bone marrow function: for example, ANC: $<1.5 \times 10^9/l$, or platelet count $<100 \times 10^9/l$, or haemoglobin <9 g/dl. Patients may be transfused to maintain haemoglobin values >9 g/dl. Exclusion also include inadequate coagulation parameters: aPTT>1.5×ULN (patients on heparin treatment must have an aPTT between 1.5-2.5×ULN), or INR>1.5. (In patients receiving anticoagulants (such as warfarin) INR must be between 2.0 and 3.0 in two consecutive measurements 1-4 days apart). Exclusions include, inadequate liver function, defined as: serum (total) bilirubin >1.5×ULN for the institution; alkaline phosphatase, AST/SGOT or ALT/SGPT>2.5×ULN (or 5×ULN in the presence of liver metastases). Exclusions include inadequate renal function, defined as serum creatinine >2.0 mg/dl or >177 µmol/l or calculated creatinine clearance <40 ml/min (by Cockroft & Gault formula) for patients intended to be treated with topotecan; or urine dipstick for proteinuria >2+. Patients with ≥2+ proteinuria on baseline dipstick analysis should undergo a 24-hour urine collection and must demonstrate ≤1 g of protein in the 24-hour urine. Alternatively, proteinuria testing can be performed according to local standards.

Prior or Concomitant Conditions or Procedures:

History or evidence upon physical/neurological examination of CNS disease unrelated to cancer, unless adequately treated with standard medical therapy (e.g. uncontrolled seizures); symptomatic CNS metastasis; pre-existing peripheral neuropathy ≥CTC grade 2 for those patients planned to receive paclitaxel; pregnant or lactating females. Serum pregnancy test to be assessed within 7 days prior to study treatment start, or within 14 days (with a confirmatory urine pregnancy test within 7 days prior to study treatment start); women of childbearing potential (defined as <2 years after last menstruation and not surgically sterile) not using highly-effective, hormonal or non-hormonal means of contraception (i.e. intrauterine contraceptive device) during the study and for 6 months after the last dose of study medication; history or evidence of thrombotic or hemorrhagic disorders; including cerebrovascular accident (CVA)/stroke or transient ischemic attack (TIA) or sub-arachnoid haemorrhage within ≤6 months prior to the first study treatment; uncontrolled hypertension (sustained systolic >150 mmHg and/or diastolic >100 mmHg despite antihypertensive therapy) or clinically significant (i.e. active) cardiovascular disease, including: myocardial infarction or unstable angina within ≤6 months prior to the first study treatment or New York Heart Association (NYHA) grade II or greater congestive heart failure (CHF) or serious cardiac arrhythmia requiring medication (with the exception of atrial fibrillation or paroxysmal supraventricular tachycardia) or peripheral vascular disease >grade 3 (i.e. symptomatic and interfering with activities of daily living requiring repair or revision). Exclusions also include left ventricular ejection fraction defined by MUGA/ECHO below the institutional lower limit of normal (only applicable for patients intended to be treated with pegylated liposomal doxorubicin); history of bowel obstruction, including sub-occlusive disease, related to the underlying disease and history of abdominal fistula, gastrointestinal perforation or intra-abdominal abscess. Evidence of recto-sigmoid involvement by pelvic examination or bowel involvement on CT scan or clinical symptoms of bowel obstruction; non-healing wound, ulcer or bone fracture; serious active infection requiring i.v. antibiotics and/or hospitalisation at study entry; known hypersensitivity to any of the study drugs or excipients; evidence of any other medical conditions (such as psychiatric illness, peptic ulcer, etc.), physical examination or laboratory findings that may interfere with the planned treatment, affect patient compliance or place the patient at high risk from treatment-related complications.

Results:

Eligible patients had ovarian cancer (measurable by RECIST 1.0 or assessable) that had progressed ≤6 mo after ≥4 cycles of platinum-based therapy. Patients with refractory ovarian cancer, history of bowel obstruction or >2 prior anticancer regimens were ineligible. After chemotherapy selection (pegylated liposomal doxorubicin [PLD], topotecan [TOP] or weekly paclitaxel [PAC]), patients were randomized to chemotherapy either alone or with bevacizumab (10 mg/kg every two weeks or 15 mg/kg every three weeks depending on chemotherapy) until progression, unacceptable toxicity or withdrawal of consent. Patients in the chemotherapy-alone arm could cross over to bevacizumab monotherapy at progression. The primary endpoint was PFS by RECIST. Secondary endpoints included objective response rate (ORR), overall survival, safety and quality of life. The design provided 80% power to detect a PFS hazard ratio (HR) of 0.7 with 2-sided log-rank test and α=0.05 after 247 events, assuming median PFS of 4.0 mo with chemotherapy and 5.7 mo with chemotherapy+bevacizumab. The sample size was increased as suggested by the IDMC; primary analysis was planned after events in 291 of 361 patients.

Between October 2009 and April 2011, 361 patients were randomized to receive selected chemotherapy (PLD: 126; PAC: 115; TOP: 120) alone or with bevacizumab. Median follow-up is 13.5 months.

TABLE 1

AURELIA PHASE III RESULTS

|  | Chemotherapy (CT) | bevacizumab + CT |
|---|---|---|
| PFS by RECIST | (N = 182) | (N = 179) |
| Events, n (%) | 166 (91) | 135 (75) |
| HR (95% CI) | 0.48 (0.38-0.60) | |
|  | Log-rank p < 0.001 | |
| Median, mo (95% CI) | 3.4 (2.2-3.7) | 6.7 (5.7-7.9) |
| ORR, % (95% CI) | 12.6 (8.0-18.4) | 30.9 (24.1-38.3) |
|  | p = 0.001 | |
|  | (N = 181) | (N = 179) |
| Selected Grade ≥3 AEs, % |  |  |
| Hypertension (Grade ≥2) | 7 | 20 |
| Proteinuria (Grade ≥2) | 1 | 11 |
| Bleeding | 1 | 1 |
| Thromboembolic event | 4 | 5 |
| Arterial | 0 | 2 |
| Venous | 4 | 3 |
| GI perforation (Grade ≥2) | 0 | 2 |
| Fistula/abscess (Grade ≥2) | 0 | 2 |
| RPLS | 0 | 1 |
| Febrile neutropenia | 1 | 1 |
| CHF | 1 | 1 |

Figure 2:
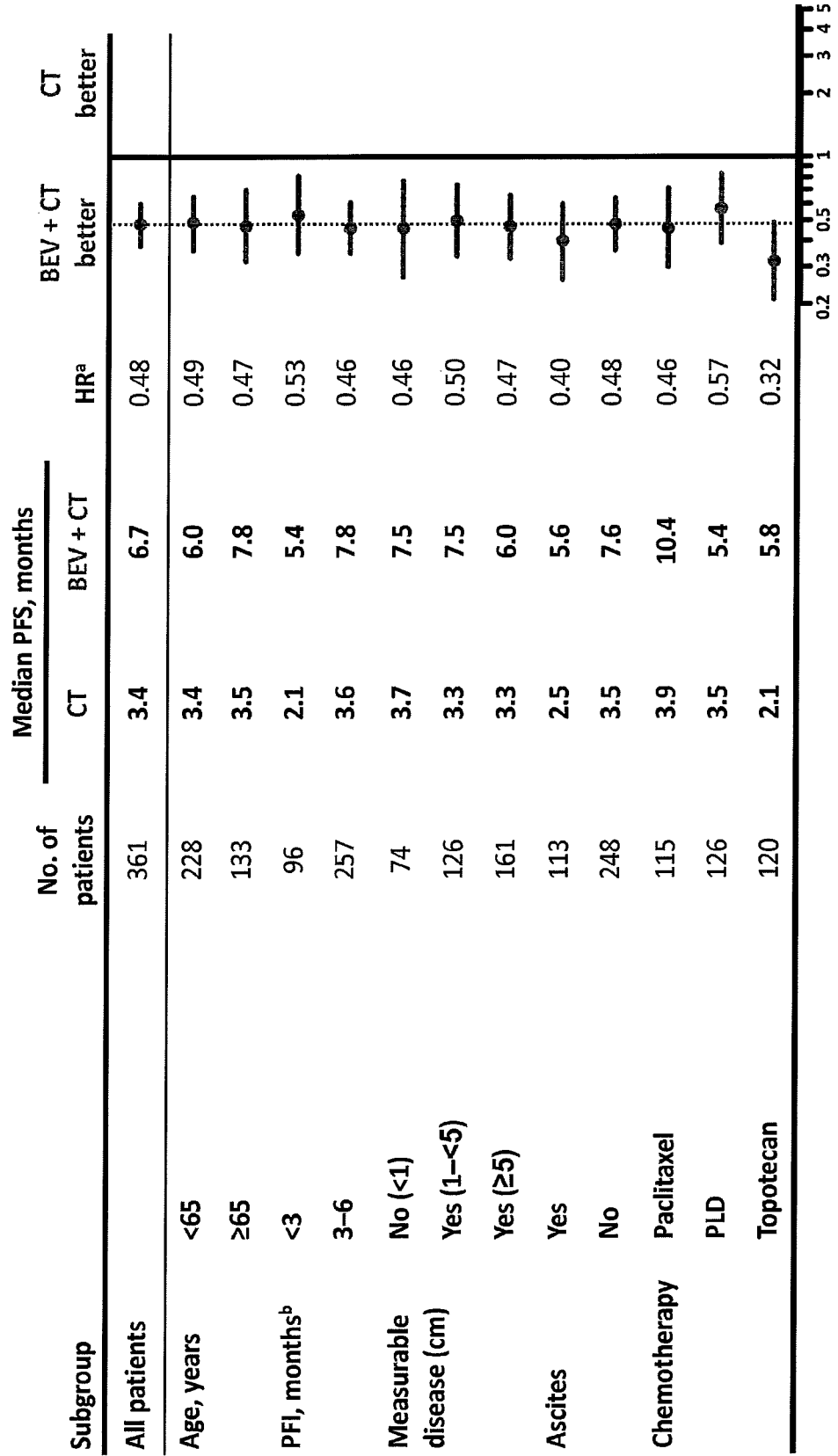
FIG. 2 shows patient stratification analysis of the progression-free survival (PFS) results from the phase III AURELIA trial which subdivides the patients in subgroups based on different risk factors and compares in which patient subgroup the bevacizumab and chemotherapy combination treatment resulted in a better PFS outcome versus chemotherapy treatment alone. CT=chemotherapy; BEV+CT=bevacizumab+chemotherapy; HR=unadjusted hazard ratio; PFI=platinum-free interval as measured in months, where a total of 8 patients' information is missing.

FIG. 2 shows the patient stratification of the trial participants by subdividing the patients in subgroups by different risk factors, e.g. age in years, either greater than or equal to 65 years in age or younger than 65 years; by patients whose platinum free interval (PFI) was less than 3 months (these are patients who typically have a worse prognostic factor as compared to other patients) or those whose PFI was between 3 to 6 months; patients who had measurable disease or tumors as measured in centimeters as indicated; patients with ascites, meaning having fluid in the abdominal cavity, typically have a more symptomatic disease and a poorer outcome as compared to those who did not; and patients who received one of the three chemotherapy regimens, either paclitaxel, PLD or topotecan, as chosen by the patient's attending physician. Regardless of which subgroup of patients was treated, the combination of bevacizumab and chemotherapy demonstrates efficacy and an increase in patient benefit as in all cases, the hazard ratios in each subgroup are aligned around 0.5 as shown on the x-axis at the bottom of the figure.

Figure 3:
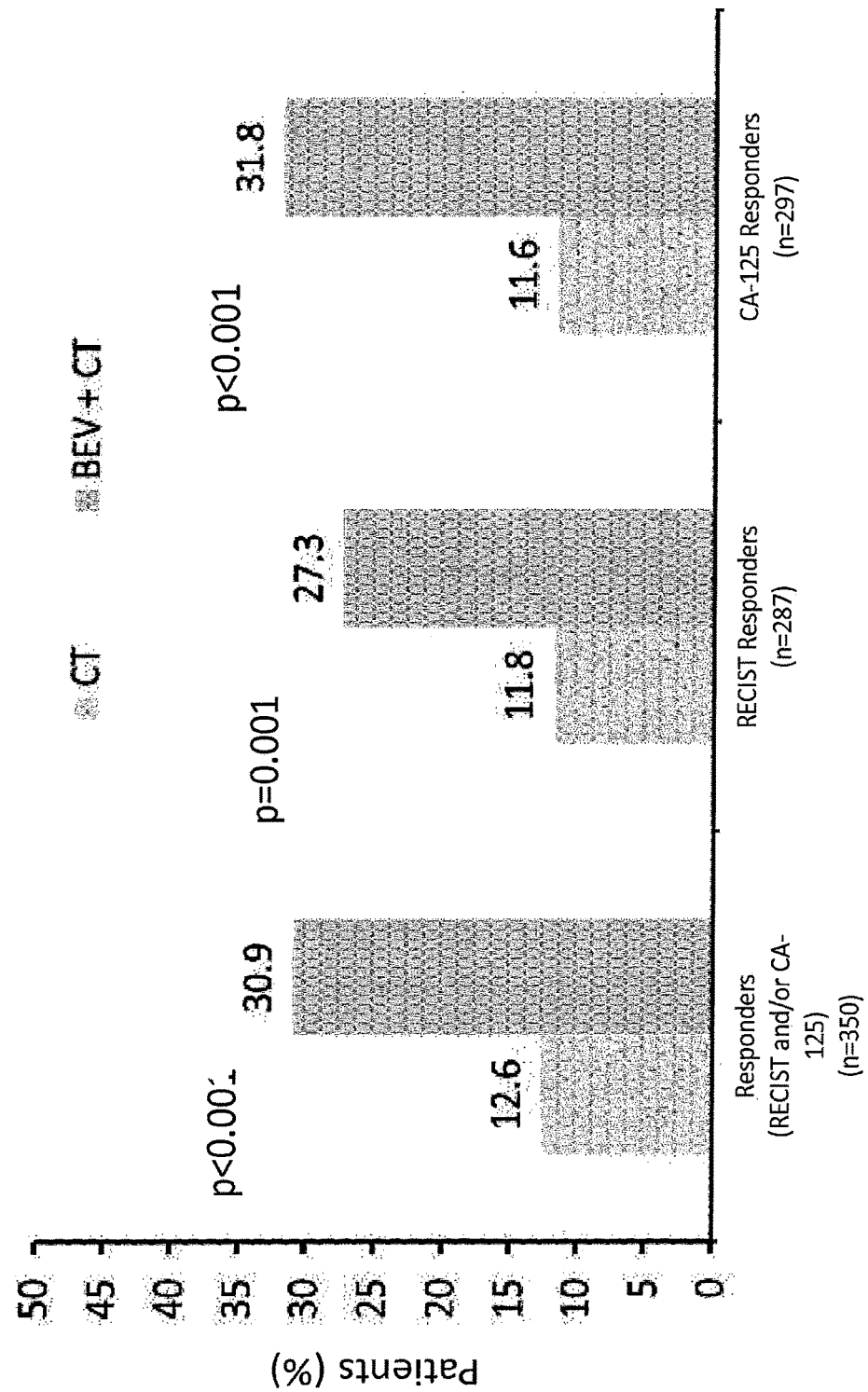
FIG. 3 shows a summary of best overall response rates (ORR), as measured by a two-sided chi-square test with Schouten correction, comparing the percent of patients who were measured by RECIST and/or CA-125 responders, RECIST responders alone, and CA-125 responders alone as between the two treatment arms, chemotherapy alone (CT) as shown in each case as the grey-stippeled bars, versus bevacizumab and chemotherapy combination (BEV+CT) as shown in each case as the grey bars. N shows the number of patients in each tested group.

FIG. 3 compares the two most common methods to measure response to therapy, either using a blood test, CA-125 or by radiography (RECIST) or combining both (RECIST+CA 125). Using all methods, the data shows that the addition of bevacizumab increased the overall response rate (ORR) as compared to those patients treated with chemotherapy alone, indicating that with the combination therapy, patient ovarian tumors appeared to shrink more than with chemotherapy alone.

Analysis by chemotherapy cohort is summarized in Table 2 below. In platinum-resistant ovarian cancer, the improvement in PFS and ORR gained by adding bevacizumab to single-agent chemotherapy was observed across all chemotherapy cohorts.

TABLE 2

AURELIA PHASE III CHEMOTHERAPY EXPOSURE AND EFFICACY

|  | PAC (n = 115) | | PLD (n = 126) | | TOP (n = 120) | |
|---|---|---|---|---|---|---|
|  | CT (n = 55) | BEV + CT (n = 60) | CT (n = 64) | BEV + CT (n = 62) | CT (n = 63) | BEV + CT (n = 57) |
| Median age, y | 60 | 60 | 62 | 63.5 | 61 | 60 |
| FIGO stage III/IV, % | 87 | 90 | 81 | 90 | 89 | 96 |
| PT-free interval <3 mo, % | 27 | 27 | 20 | 27 | 25 | 26 |
| Median No. of CT | 4 | 6 | 3 | 4 | 3 | 6 |
| cycles (range) | (1-15) | (1-13) | (1-17) | (1-11) | (1-11) | (1-14) |
| PFS |  |  |  |  |  |  |
| Events, % | 89 | 62 | 95 | 87 | 89 | 77 |
| Median, mo | 3.9 | 10.4 | 3.5 | 5.4 | 2.1 | 5.8 |
| HR | 0.46 | | 0.57 | | 0.32 | |
| (95% CI)[a] | (0.30-0.71) | | (0.39-0.83) | | (0.21-0.49) | |
| ORR, % | 28.8 | 51.7 | 7.9 | 18.3 | 3.3 | 22.8 |
| Difference | 22.9 | | 10.4 | | 19.5 | |
| (95% CI) | (3.9-41.8) | | (−2.4 to 23.2) | | (6.7-32.3) | |

[a]Unstratified
ORR = overall response rate (RECIST and/or CA-125)

In platinum-resistant ovarian cancer, the improvement in PFS and ORR gained by adding bevacizumab to single-agent chemotherapy was observed across all chemotherapy cohorts. Increased chemotherapy exposure associated with prolonged PFS accounts for some increase in cumulative chemotherapy toxicity.

AURELIA is the first randomized trial of bevacizumab in platinum-resistant ovarian cancer. It has been shown that bevacizumab and chemotherapy provides statistically significant and clinically meaningful improvement in ORR and PFS versus chemotherapy alone. Careful patient screening minimizes the risk of bevacizumab adverse events. This is the first phase III trial in platinum-resistant ovarian cancer to show benefit with a targeted therapy and improved outcome with a combination versus monotherapy.

We claim:

1. A method of treating a human patient diagnosed with a platinum-resistant ovarian cancer, fallopian tube cancer, or primary peritoneal carcinoma, comprising administering to said patient an effective amount of bevacizumab and a chemotherapeutic, wherein said patient received two or fewer prior anti-cancer regimens, wherein said treatment prolongs said patient's median progression-free survival time as compared to a platinum-resistant ovarian cancer, fallopian tube cancer, or primary peritoneal carcinoma patient receiving said chemotherapeutic alone, and wherein said chemotherapeutic is paclitaxel.

2. The method of claim 1, wherein said platinum-resistant ovarian cancer is an epithelial ovarian cancer.

3. The method of claim 1, wherein said patient is not refractory to previous platinum treatment.

4. The method of claim 1, wherein said patient has measurable disease according to Response Evaluation Criteria in Solid Tumor (RECIST) 1.0 or Cancer Antigen-125 (CA-125) assessable disease according to the Gynecologic Cancer Intergroup (GCIG) criteria.

5. The method of claim 1, wherein said patient has an Eastern Cooperative Oncology Group (ECOG) performance status of 0-2.

6. The method of claim 1, wherein said patient has a life expectancy of at least 12 weeks.

7. The method of claim 1, wherein said effective amount of said paclitaxel is administered at 80 mg/m2 as a 1 hour intravenous infusion on days 1, 8, 15 and 22 q4w.

8. The method of claim 1, wherein said effective amount of said bevacizumab is 10 mg/kg intravenously every two weeks.

9. The method of claim 1, wherein said effective amount of said bevacizumab is 15 mg/kg intravenously every three weeks.

10. The method of claim 1, wherein said effective amount of said bevacizumab is administered initially intravenously over 90 minutes, with subsequent infusions over 60 minutes and then 30 minutes.

11. The method of claim 1, wherein said bevacizumab is administered first to said patient at the first cycle.

12. The method of claim 11, wherein subsequent administrations of said bevacizumab are either prior to or after said chemotherapeutic.

13. The method of claim 1, wherein said bevacizumab is administered concurrently with said chemotherapeutic.

14. The method of claim 1, wherein said patient is less than 65 years old.

15. The method of claim 1, wherein said patient is equal to or greater than 65 years old.

16. The method of claim 1, wherein said patient has a platinum free interval (PFI) of less than 3 months.

17. The method of claim 1, wherein said patient has a PFI of 3 to 6 months.

18. The method of claim 1, wherein said patient has abdominal ascites.

19. The method of claim 1, wherein said patient does not have abdominal ascites.

20. The method of claim 1, wherein the progression free survival is prolonged by at least about three months as compared to a platinum-resistant ovarian cancer, fallopian tube cancer, or primary peritoneal carcinoma patient receiving said chemotherapeutic alone.

* * * * *